(12) United States Patent
Chen et al.

(10) Patent No.: US 8,247,388 B2
(45) Date of Patent: Aug. 21, 2012

(54) ROLE OF MIRNA IN T CELL LEUKEMIA

(75) Inventors: Chang-Zheng Chen, Stanford, CA (US); Tin Mao, Alameda, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 40 days.

(21) Appl. No.: 12/455,898

(22) Filed: Jun. 8, 2009

(65) Prior Publication Data
US 2010/0048674 A1 Feb. 25, 2010

Related U.S. Application Data

(60) Provisional application No. 61/131,208, filed on Jun. 6, 2008.

(51) Int. Cl.
*A61K 48/00* (2006.01)
(52) U.S. Cl. ...... 514/44; 536/24.5; 536/24.31; 536/24.1
(58) Field of Classification Search .................. None
See application file for complete search history.

(56) References Cited

U.S. PATENT DOCUMENTS

| | | |
|---|---|---|
| 2005/0256072 A1 | 11/2005 | Aronin et al. |
| 2005/0260648 A1 | 11/2005 | Huffel et al. |
| 2005/0261218 A1 | 11/2005 | Esau et al. |
| 2006/0019286 A1 | 1/2006 | Horvitz et al. |
| 2006/0057595 A1 | 3/2006 | Lao et al. |
| 2006/0099619 A1 | 5/2006 | Remacle et al. |
| 2006/0105360 A1 | 5/2006 | Croce et al. |
| 2006/0134639 A1 | 6/2006 | Huffel et al. |
| 2006/0185027 A1 | 8/2006 | Bartel et al. |
| 2008/0200416 A1 | 8/2008 | Li et al. |

OTHER PUBLICATIONS

Li et al. mir-181 is an intrinsic modulator of T cell sensitivity and selection. Cell 129, 147-161, 2007.*
Debernardi et al. MicroRNA mir-181a correlates with morphological sub-class of acute myeloid leukemia and the expression of its target genes in global genome-wide analysis. Leukemia 2007, vol. 21:912-916.*
Chen et al. MicroRNAs modulate hematopoietic lineage differentiation. Science 2004, vol. 303: 83-86.*
Zanette et al. Brazillian Journal of Medical and Biological Research 2007: 1435-1440.*
Aifantis; et al., "Molecular pathogenesis of T-cell leukaemia and lymphoma", Nature (2008), 8:380-390.
Krutzfeldt; et al., "Silencing of microRNAs in vivo with 'antogomirs'", Nature (2005), 438:685-689.
Liu; et al., "Pre-miRNA Loop Nucleotides Control the Distinct Activities of mir-181a-1 and mir-181c in Early T Cell Development", PLoS One (2008), 3(10):e3592-e3592.

* cited by examiner

*Primary Examiner* — Kimberly Chong
(74) *Attorney, Agent, or Firm* — Bozicevic, Field & Francis LLP; Pamela J. Sherwood

(57) ABSTRACT

The ability of miR-181a to support active signaling between Notch and pre-TCR pathways by coordinately dampening negative regulators of these pathways allows the use of miR-181a as a therapeutic target for T-ALL.

7 Claims, 24 Drawing Sheets
(4 of 24 Drawing Sheet(s) Filed in Color)

FIGURE 2
(B) Putative miR-181a target sites on mouse Nrarp
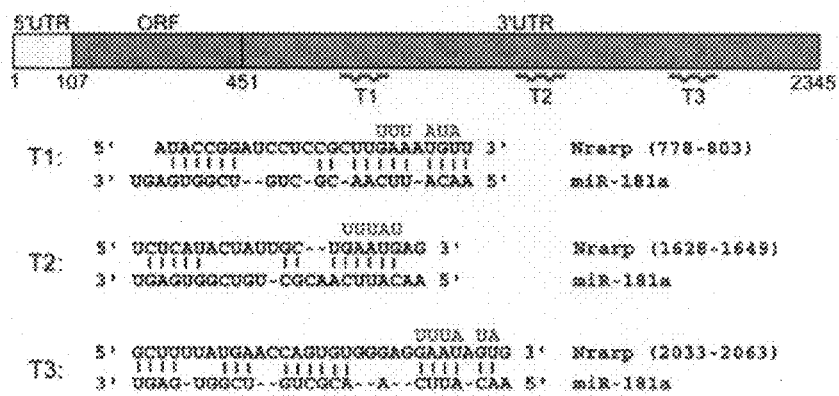
(C) 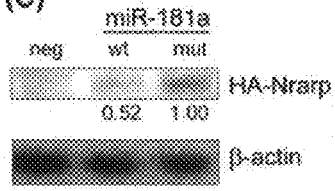
(D) 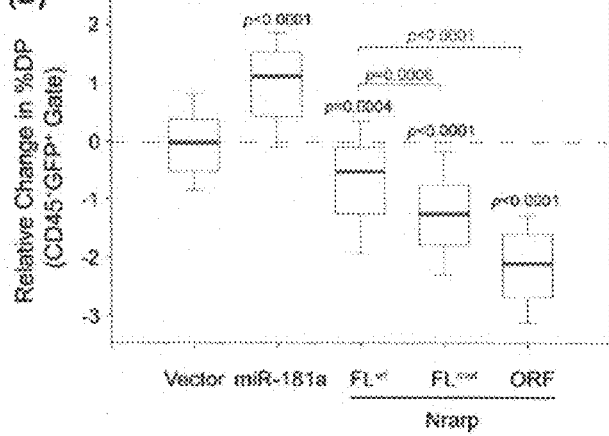

Figure 4.
(A)
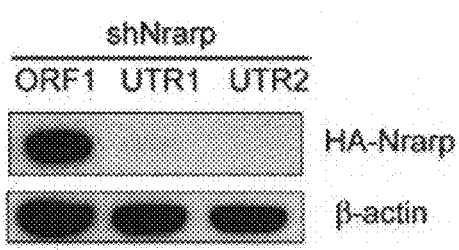
(B)
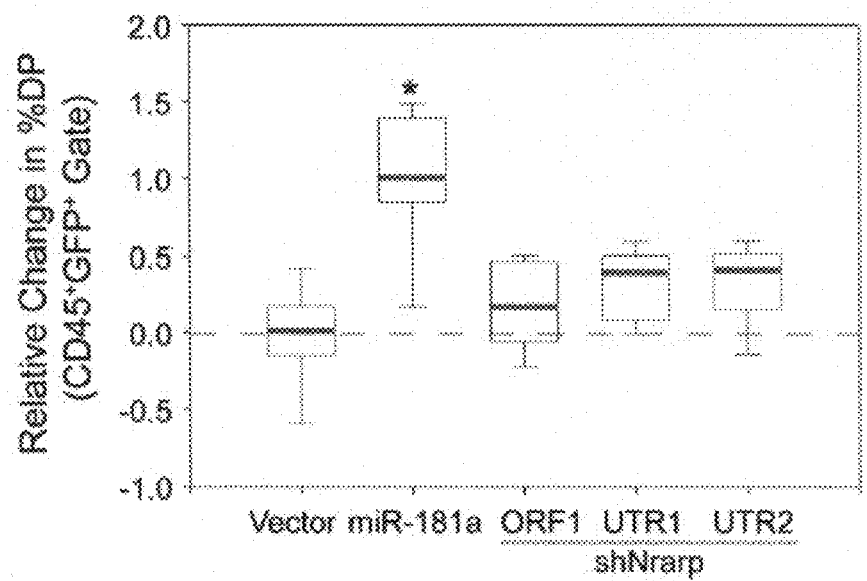

Figure 5.
(A)
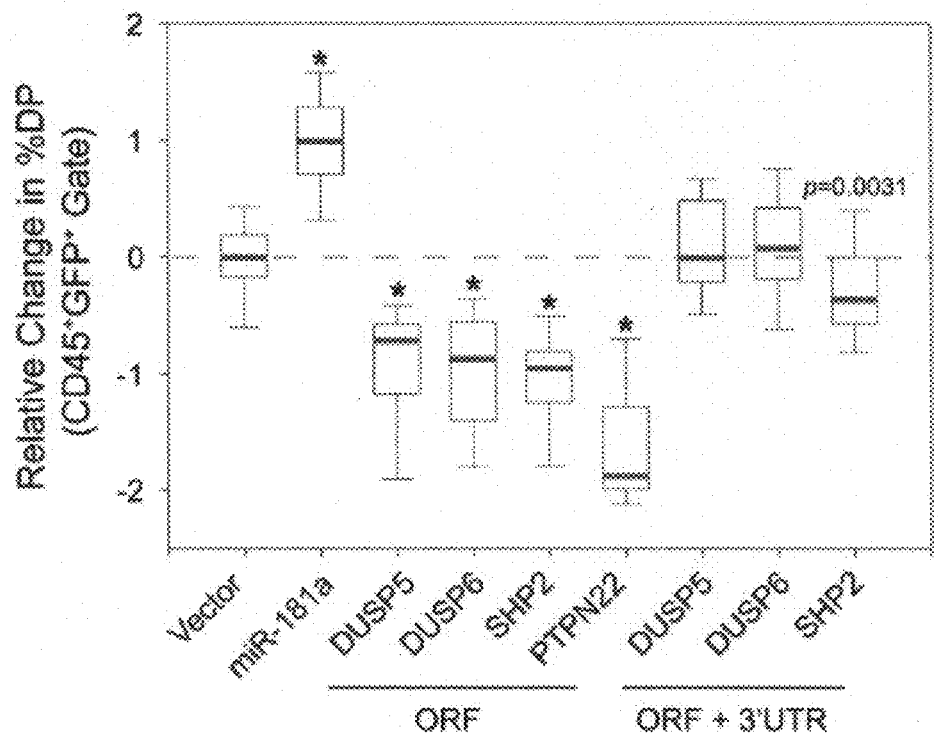
(B)
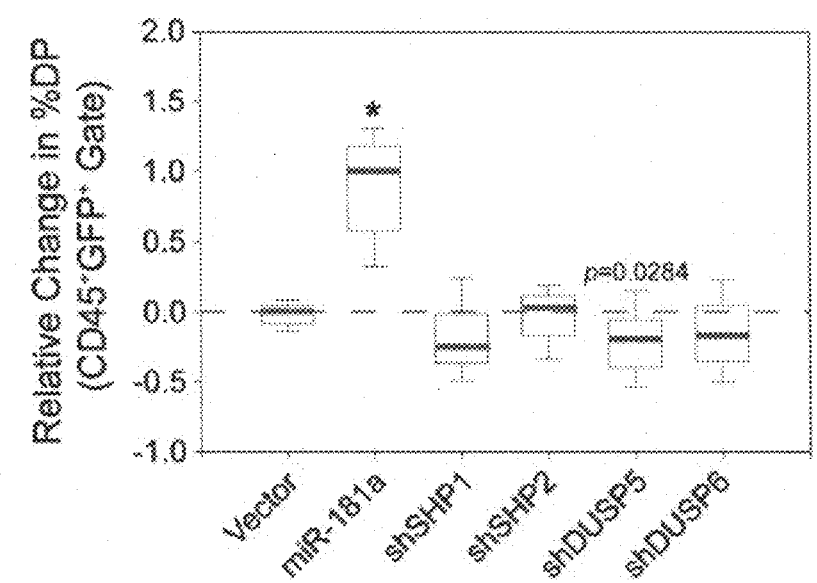

Expressing miR-181a or shRNA from RNA Polymerase III

FIGURE 9
(A) OP9-DL1 co-culture assay initiated by sorted DN thymocytes
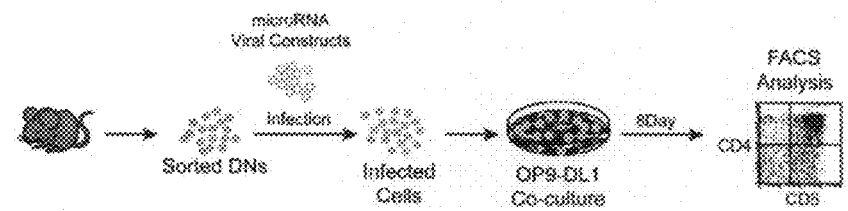
(B) OP9-DL1 co-culture assay initiated by total thymocytes
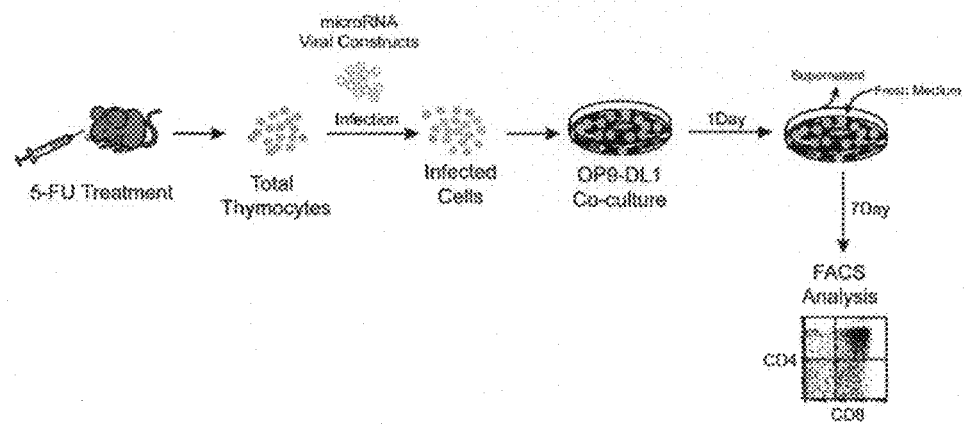

FIGURE 10
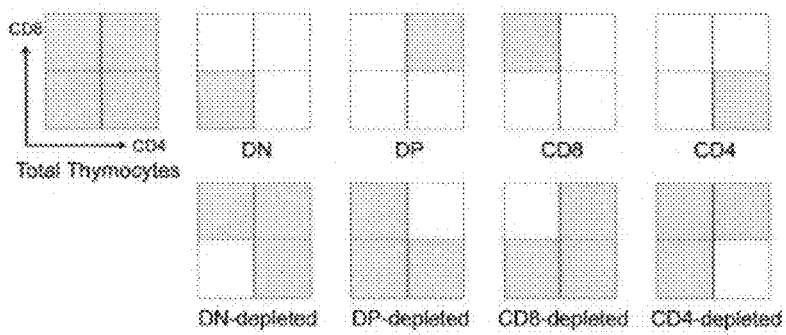
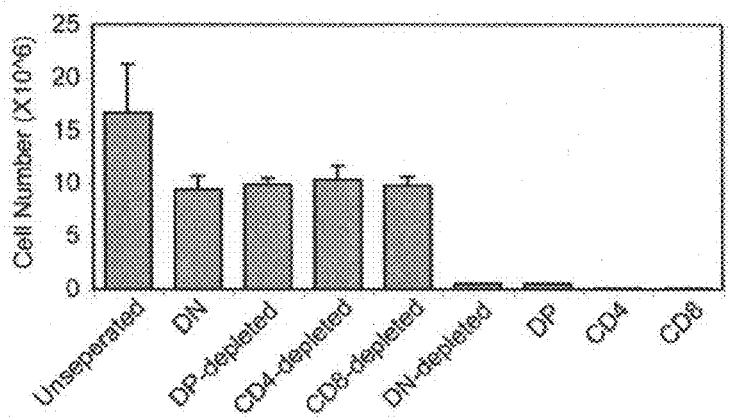
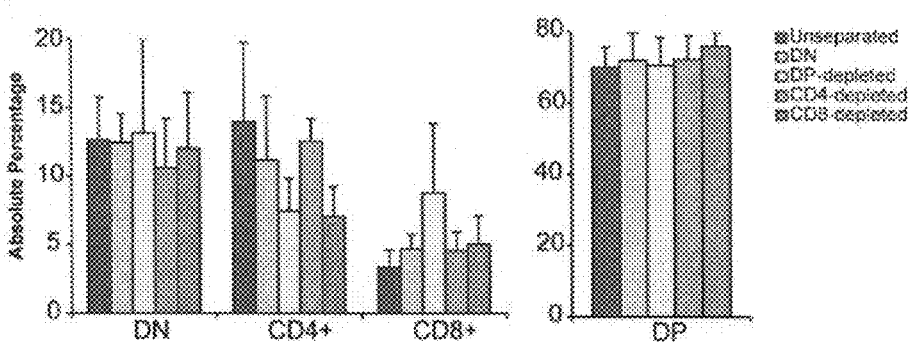

FIGURE 13
(A) Putative miR-181a target sites on Numb (AK004553)
(B) Putative miR-181a target sites on Numblike (NM_010950)
(C) Putative miR-181a target sites on Hes6 (BC012897)
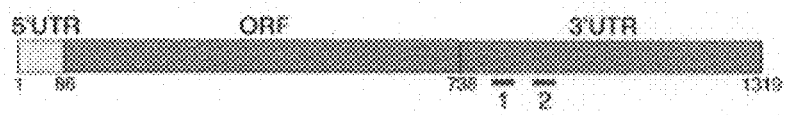
(D) Putative miR-181a target sites on LFNG (AK004642)
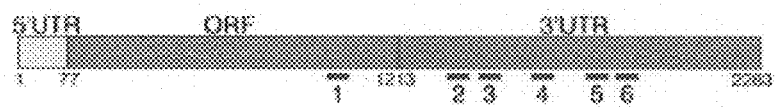

miR-181a:Nrarp Epistatic Interactions

FIGURE 16
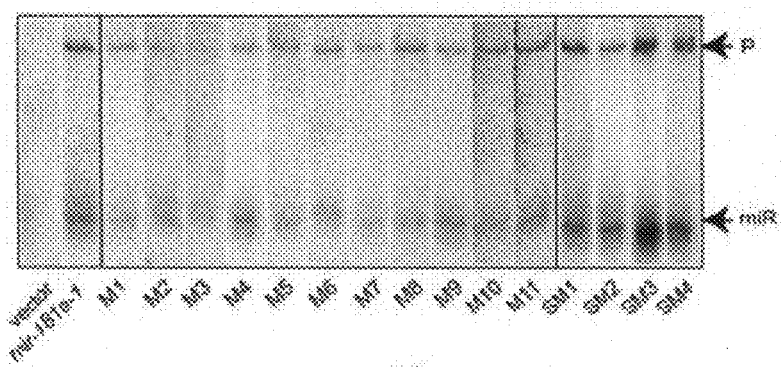
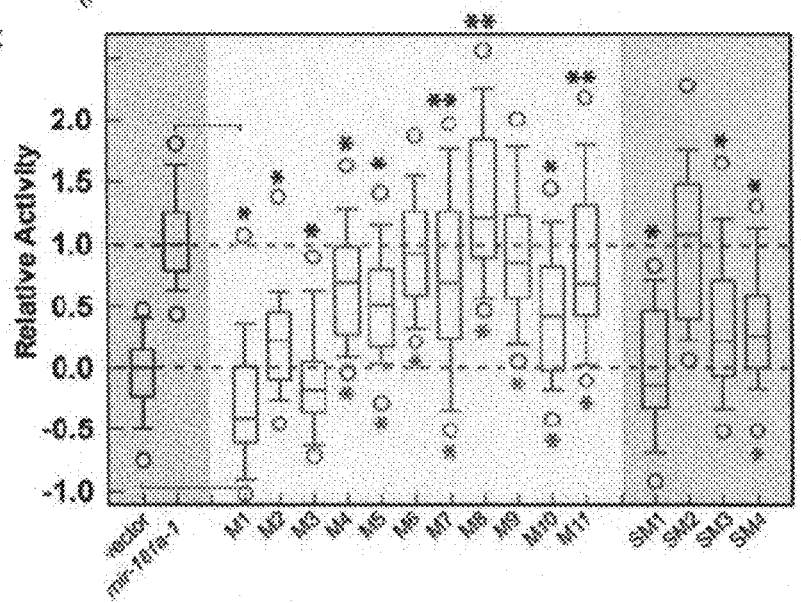

FIGURE 22
(A) 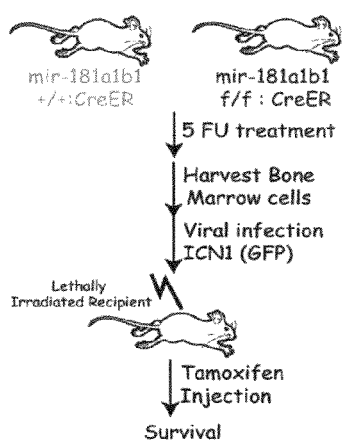
(B) 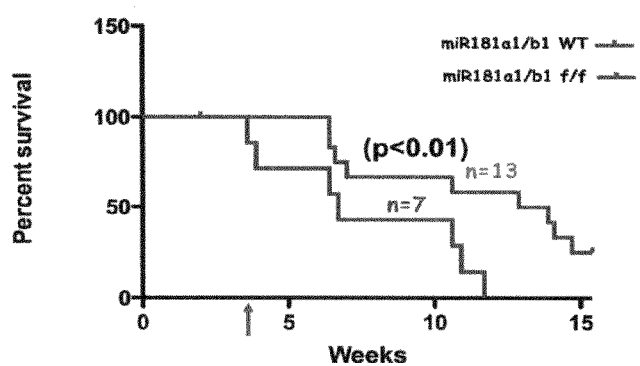

SEQUENCE LISTING

<160> NUMBER OF SEQ ID NOS: 70

<210> SEQ ID NO 1
<211> LENGTH: 23
<212> TYPE: RNA
<213> ORGANISM: Mus musculus

```
<220> FEATURE:
<223> OTHER INFORMATION: Synthesized sequence

<400> SEQUENCE: 1
aacauucaac gcugucggug agu                                          23

<210> SEQ ID NO 2
<211> LENGTH: 23
<212> TYPE: RNA
<213> ORGANISM: Artificial Sequence
<220> FEATURE:
<223> OTHER INFORMATION: Synthesized sequence

<400> SEQUENCE: 2
auauaaaaac gcugucggug agu                                          23

<210> SEQ ID NO 3
<211> LENGTH: 26
<212> TYPE: RNA
<213> ORGANISM: Mus musculus

<400> SEQUENCE: 3
auaccggauc cuccgcuuga aauguu                                       26

<210> SEQ ID NO 4
<211> LENGTH: 22
<212> TYPE: RNA
<213> ORGANISM: Mus musculus

<400> SEQUENCE: 4
ucucauacua uugcugaaug ag                                           22

<210> SEQ ID NO 5
<211> LENGTH: 31
<212> TYPE: RNA
<213> ORGANISM: Mus musculus

<400> SEQUENCE: 5
gcuuuuauga accagugugg gaggaauagu g                                 31

<210> SEQ ID NO 6
<211> LENGTH: 23
<212> TYPE: RNA
<213> ORGANISM: Artificial Sequence
<220> FEATURE:
<223> OTHER INFORMATION: Synthesized sequence

<400> SEQUENCE: 6
auaauucaac gcugucggug agu                                          23

<210> SEQ ID NO 7
<211> LENGTH: 23
<212> TYPE: RNA
<213> ORGANISM: Artificial Sequence
<220> FEATURE:
<223> OTHER INFORMATION: Synthesized sequence

<400> SEQUENCE: 7
aacuaucaac gcugucggug agu                                          23

<210> SEQ ID NO 8
<211> LENGTH: 23
<212> TYPE: RNA
<213> ORGANISM: Artificial Sequence
<220> FEATURE:
<223> OTHER INFORMATION: Synthesized sequence
```

```
<400> SEQUENCE: 8
aacauaaaac gcugucggug agu                                              23

<210> SEQ ID NO 9
<211> LENGTH: 23
<212> TYPE: RNA
<213> ORGANISM: Artificial Sequence
<220> FEATURE:
<223> OTHER INFORMATION: Synthesized sequence

<400> SEQUENCE: 9
aacauucuuc gcugucggug agu                                              23

<210> SEQ ID NO 10
<211> LENGTH: 23
<212> TYPE: RNA
<213> ORGANISM: Artificial Sequence
<220> FEATURE:
<223> OTHER INFORMATION: Synthesized sequence

<400> SEQUENCE: 10
aacauucaaa ccugucggug agu                                              23

<210> SEQ ID NO 11
<211> LENGTH: 23
<212> TYPE: RNA
<213> ORGANISM: Artificial Sequence
<220> FEATURE:
<223> OTHER INFORMATION: Synthesized sequence

<400> SEQUENCE: 11
aacauucaac gaagucggug agu                                              23

<210> SEQ ID NO 12
<211> LENGTH: 23
<212> TYPE: RNA
<213> ORGANISM: Artificial Sequence
<220> FEATURE:
<223> OTHER INFORMATION: Synthesized sequence

<400> SEQUENCE: 12
aacauucaac gcucacggug agu                                              23

<210> SEQ ID NO 13
<211> LENGTH: 23
<212> TYPE: RNA
<213> ORGANISM: Artificial Sequence
<220> FEATURE:
<223> OTHER INFORMATION: Synthesized sequence

<400> SEQUENCE: 13
aacauucaac gcuguacgug agu                                              23

<210> SEQ ID NO 14
<211> LENGTH: 23
<212> TYPE: RNA
<213> ORGANISM: Artificial Sequence
<220> FEATURE:
<223> OTHER INFORMATION: Synthesized sequence

<400> SEQUENCE: 14
aacauucaac gcugucgcag agu                                              23

<210> SEQ ID NO 15
<211> LENGTH: 23
```

```
<212> TYPE: RNA
<213> ORGANISM: Artificial Sequence
<220> FEATURE:
<223> OTHER INFORMATION: Synthesized sequence

<400> SEQUENCE: 15
aacauucaac gcugucgguc ugu                                                 23

<210> SEQ ID NO 16
<211> LENGTH: 23
<212> TYPE: RNA
<213> ORGANISM: Artificial Sequence
<220> FEATURE:
<223> OTHER INFORMATION: Synthesized sequence

<400> SEQUENCE: 16
aacauucaac gcugucggug aca                                                 23

<210> SEQ ID NO 17
<211> LENGTH: 23
<212> TYPE: RNA
<213> ORGANISM: Artificial Sequence
<220> FEATURE:
<223> OTHER INFORMATION: Synthesized sequence

<400> SEQUENCE: 17
aacauucuua caacacggug agu                                                 23

<210> SEQ ID NO 18
<211> LENGTH: 23
<212> TYPE: RNA
<213> ORGANISM: Artificial Sequence
<220> FEATURE:
<223> OTHER INFORMATION: Synthesized sequence

<400> SEQUENCE: 18
aacauucaac gcuguaccac uca                                                 23

<210> SEQ ID NO 19
<211> LENGTH: 23
<212> TYPE: RNA
<213> ORGANISM: Artificial Sequence
<220> FEATURE:
<223> OTHER INFORMATION: Synthesized sequence

<400> SEQUENCE: 19
aacauucuua caacaaccac uca                                                 23

<210> SEQ ID NO 20
<211> LENGTH: 22
<212> TYPE: RNA
<213> ORGANISM: Artificial Sequence
<220> FEATURE:
<223> OTHER INFORMATION: Synthesized sequence

<400> SEQUENCE: 20
aacauucaac cugucgguga gu                                                  22

<210> SEQ ID NO 21
<211> LENGTH: 62
<212> TYPE: RNA
<213> ORGANISM: Artificial Sequence
<220> FEATURE:
<223> OTHER INFORMATION: Synthesized sequence

<400> SEQUENCE: 21
aacauucaac gcugucggug aguuuggaau ucaaauaaaa accaucgacc guugauugua         60
``` cc                                                                  62

<210> SEQ ID NO 22
<211> LENGTH: 61
<212> TYPE: RNA
<213> ORGANISM: Artificial Sequence
<220> FEATURE:
<223> OTHER INFORMATION: Synthesized sequence

<400> SEQUENCE: 22
aacauucaac cugucgguga guuugggcag cucagacaaa ccaucgaccg uugaguggac    60
c                                                                   61

<210> SEQ ID NO 23
<211> LENGTH: 61
<212> TYPE: RNA
<213> ORGANISM: Artificial Sequence
<220> FEATURE:
<223> OTHER INFORMATION: Synthesized sequence

<400> SEQUENCE: 23
aacauucaac cugucgguga guuggaauu caaauaaaaa ccaucgaccg uugaguggac    60
c                                                                   61

<210> SEQ ID NO 24
<211> LENGTH: 62
<212> TYPE: RNA
<213> ORGANISM: Artificial Sequence
<220> FEATURE:
<223> OTHER INFORMATION: Synthesized sequence

<400> SEQUENCE: 24
aacauucaac gcugucggug aguuugggca gcucagacaa accuacgacc guugauugua    60
cc                                                                  62

<210> SEQ ID NO 25
<211> LENGTH: 61
<212> TYPE: RNA
<213> ORGANISM: Artificial Sequence
<220> FEATURE:
<223> OTHER INFORMATION: Synthesized sequence

<400> SEQUENCE: 25
aacauucaac gcugucggug auuugggcag cucagacaaa caucgacccg uugaguggac    60
c                                                                   61

<210> SEQ ID NO 26
<211> LENGTH: 61
<212> TYPE: RNA
<213> ORGANISM: Artificial Sequence
<220> FEATURE:
<223> OTHER INFORMATION: Synthesized sequence

<400> SEQUENCE: 26
aacauucaac gcugucggug aguugggcag cucagacaac caucgacccg uugaguggac    60
c                                                                   61

<210> SEQ ID NO 27
<211> LENGTH: 61
<212> TYPE: RNA
<213> ORGANISM: Artificial Sequence
<220> FEATURE:
<223> OTHER INFORMATION: Synthesized sequence

<400> SEQUENCE: 27
aacauucaac cugucgguga guuugggcag cucagacaaa ccaucgaccg uugaguggac    60
c                                                                    61

<210> SEQ ID NO 28
<211> LENGTH: 62
<212> TYPE: RNA
<213> ORGANISM: Artificial Sequence
<220> FEATURE:
<223> OTHER INFORMATION: Synthesized sequence

<400> SEQUENCE: 28
aacauucaac gcugucggug aguuuggaau ucaaauaaaa accauccacc guugauugua    60
cc                                                                   62

<210> SEQ ID NO 29
<211> LENGTH: 62
<212> TYPE: RNA
<213> ORGANISM: Artificial Sequence
<220> FEATURE:
<223> OTHER INFORMATION: Synthesized sequence

<400> SEQUENCE: 29
aacauucaac gcugucggug aguuugggca gcucagacaa accaucgacc guugauugua    60
cc                                                                   62

<210> SEQ ID NO 30
<211> LENGTH: 61
<212> TYPE: RNA
<213> ORGANISM: Artificial Sequence
<220> FEATURE:
<223> OTHER INFORMATION: Synthesized sequence

<400> SEQUENCE: 30
aacauucaac cugucgguga guuuggaauu caaauaaaaa ccaucgaccg uugaguggac    60
c                                                                    61

<210> SEQ ID NO 31
<211> LENGTH: 62
<212> TYPE: RNA
<213> ORGANISM: Artificial Sequence
<220> FEATURE:
<223> OTHER INFORMATION: Synthesized sequence

<400> SEQUENCE: 31
aacauucaac gcugucggug aguuuccaau ucaaauaaaa accaucgacc guugauugua    60
cc                                                                   62

<210> SEQ ID NO 32
<211> LENGTH: 62
<212> TYPE: RNA
<213> ORGANISM: Artificial Sequence
<220> FEATURE:
<223> OTHER INFORMATION: Synthesized sequence

<400> SEQUENCE: 32
aacauucaac gcugucggug aguuugguuu ucaaauaaaa accaucgacc guugauugua    60
cc                                                                   62

<210> SEQ ID NO 33
<211> LENGTH: 62

```
<212> TYPE: RNA
<213> ORGANISM: Artificial Sequence
<220> FEATURE:
<223> OTHER INFORMATION: Synthesized sequence

<400> SEQUENCE: 33
aacauucaac gcugucggug aguuuggaaa acaaauaaaa accaucgacc guugauugua    60
cc                                                                  62

<210> SEQ ID NO 34
<211> LENGTH: 62
<212> TYPE: RNA
<213> ORGANISM: Artificial Sequence
<220> FEATURE:
<223> OTHER INFORMATION: Synthesized sequence

<400> SEQUENCE: 34
aacauucaac gcugucggug aguuuggaau uguaauaaaa accaucgacc guugauugua    60
cc                                                                  62

<210> SEQ ID NO 35
<211> LENGTH: 62
<212> TYPE: RNA
<213> ORGANISM: Artificial Sequence
<220> FEATURE:
<223> OTHER INFORMATION: Synthesized sequence

<400> SEQUENCE: 35
aacauucaac gcugucggug aguuuggaau ucacguaaaa accaucgacc guugauugua    60
cc                                                                  62

<210> SEQ ID NO 36
<211> LENGTH: 62
<212> TYPE: RNA
<213> ORGANISM: Artificial Sequence
<220> FEATURE:
<223> OTHER INFORMATION: Synthesized sequence

<400> SEQUENCE: 36
aacauucaac gcugucggug aguuuggaau ucaaauaaa accaucgacc guugauugua     60
cc                                                                  62

<210> SEQ ID NO 37
<211> LENGTH: 22
<212> TYPE: RNA
<213> ORGANISM: Mus musculus

<400> SEQUENCE: 37
aacauucauu gcugucggug gg                                             22

<210> SEQ ID NO 38
<211> LENGTH: 24
<212> TYPE: RNA
<213> ORGANISM: Mus musculus

<400> SEQUENCE: 38
aacauucauu gugucggug gguu                                            24

<210> SEQ ID NO 39
<211> LENGTH: 60
<212> TYPE: RNA
<213> ORGANISM: Mus musculus

<400> SEQUENCE: 39
```

-continued aacauucaac gcugucggug aguuuggaau ucaaauaaaa accaucgacc guugauugua    60

<210> SEQ ID NO 40
<211> LENGTH: 64
<212> TYPE: RNA
<213> ORGANISM: Mus musculus

<400> SEQUENCE: 40
aacauucaac gcugucggug aguuuggaau ucaaaaacaa aaaaccauc gaccguugau    60 ugua                                                                64

<210> SEQ ID NO 41
<211> LENGTH: 60
<212> TYPE: RNA
<213> ORGANISM: Mus musculus

<400> SEQUENCE: 41
aacauucauu gcugucggug gguugaacug uguagaaaag cucacugaac aaugaaugca    60

<210> SEQ ID NO 42
<211> LENGTH: 58
<212> TYPE: RNA
<213> ORGANISM: Mus musculus

<400> SEQUENCE: 42
aacauucauu gcugucggug gguuugaaug ucaaccaacu cacugaucaa ugaaugca     58

<210> SEQ ID NO 43
<211> LENGTH: 59
<212> TYPE: RNA
<213> ORGANISM: Mus musculus

<400> SEQUENCE: 43
aacauucaac cugucgguga guuugggcag cucagacaaa ccaucgaccg uugagugga    59

<210> SEQ ID NO 44
<211> LENGTH: 62
<212> TYPE: RNA
<213> ORGANISM: Mus musculus

<400> SEQUENCE: 44
aacauucauu guugucggug gguugugagg aggcagccag acccaccggg ggaugaaugu    60
ca                                                                  62

<210> SEQ ID NO 45
<211> LENGTH: 22
<212> TYPE: DNA
<213> ORGANISM: Bos taurus

<400> SEQUENCE: 45
aacattcaac gctgtcggtg ag                                             22

<210> SEQ ID NO 46
<211> LENGTH: 22
<212> TYPE: RNA
<213> ORGANISM: Bos taurus

<400> SEQUENCE: 46
aacauucaac gcugucggug ag                                             22

<210> SEQ ID NO 47
<211> LENGTH: 22

```
<212> TYPE: DNA
<213> ORGANISM: Macaca nemestrina

<400> SEQUENCE: 47
aacattcaac gctgtcggtg ag                                              22

<210> SEQ ID NO 48
<211> LENGTH: 22
<212> TYPE: RNA
<213> ORGANISM: Macaca nemestrina

<400> SEQUENCE: 48
aacauucaac gcugucggug ag                                              22

<210> SEQ ID NO 49
<211> LENGTH: 22
<212> TYPE: DNA
<213> ORGANISM: Saguinus labiatus

<400> SEQUENCE: 49
aacattcaac gctgtcggtg ag                                              22

<210> SEQ ID NO 50
<211> LENGTH: 22
<212> TYPE: RNA
<213> ORGANISM: Saguinus labiatus

<400> SEQUENCE: 50
aacauucaac gcugucggug ag                                              22

<210> SEQ ID NO 51
<211> LENGTH: 22
<212> TYPE: DNA
<213> ORGANISM: Macaca mulatta

<400> SEQUENCE: 51
aacattcaac gctgtcggtg ag                                              22

<210> SEQ ID NO 52
<211> LENGTH: 22
<212> TYPE: RNA
<213> ORGANISM: Macaca mulatta

<400> SEQUENCE: 52
aacauucaac gcugucggug ag                                              22

<210> SEQ ID NO 53
<211> LENGTH: 22
<212> TYPE: DNA
<213> ORGANISM: Pan troglodytes

<400> SEQUENCE: 53
aacattcaac gctgtcggtg ag                                              22

<210> SEQ ID NO 54
<211> LENGTH: 22
<212> TYPE: RNA
<213> ORGANISM: Pan troglodytes

<400> SEQUENCE: 54
aacauucaac gcugucggug ag                                              22

<210> SEQ ID NO 55
<211> LENGTH: 22
```

```
<212> TYPE: DNA
<213> ORGANISM: Pan paniscus

<400> SEQUENCE: 55
aacattcaac gctgtcggtg ag                                               22

<210> SEQ ID NO 56
<211> LENGTH: 22
<212> TYPE: RNA
<213> ORGANISM: Pan paniscus

<400> SEQUENCE: 56
aacauucaac gcugucggug ag                                               22

<210> SEQ ID NO 57
<211> LENGTH: 22
<212> TYPE: DNA
<213> ORGANISM: Gorilla gorilla

<400> SEQUENCE: 57
aacattcaac gctgtcggtg ag                                               22

<210> SEQ ID NO 58
<211> LENGTH: 22
<212> TYPE: RNA
<213> ORGANISM: Gorilla gorilla

<400> SEQUENCE: 58
aacauucaac gcugucggug ag                                               22

<210> SEQ ID NO 59
<211> LENGTH: 23
<212> TYPE: DNA
<213> ORGANISM: Homo sapiens

<400> SEQUENCE: 59
aacattcaac gctgtcggtg agt                                              23

<210> SEQ ID NO 60
<211> LENGTH: 23
<212> TYPE: RNA
<213> ORGANISM: Homo sapiens

<400> SEQUENCE: 60
aacauucaac gcugucggug agu                                              23

<210> SEQ ID NO 61
<211> LENGTH: 23
<212> TYPE: DNA
<213> ORGANISM: Mus musculus

<400> SEQUENCE: 61
aacattcaac gctgtcggtg agt                                              23

<210> SEQ ID NO 62
<211> LENGTH: 281
<212> TYPE: DNA
<213> ORGANISM: Homo sapiens

<400> SEQUENCE: 62
tgagttttga ggttgcttca gtgaacattc aacgctgtcg gtgagtttgg aattaaaatc      60
aaaaccatcg accgttgatt gtaccctatg gctaaccatc atctactcca tggtgctcag     120
aattcgctga agacaggaaa ccaaaggtgg acacaccagg actttctctt ccctgtgcag     180
```

| | |
|---|---|
| agattatttt ttaaaaggtc acaatcaaca ttcattgctg tcggtgggtt gaactgtgtg | 240 |
| gacaagctca ctgaacaatg aatgcaactg tggccccgct t | 281 |

<210> SEQ ID NO 63
<211> LENGTH: 110
<212> TYPE: DNA
<213> ORGANISM: Homo sapiens

<400> SEQUENCE: 63

| | |
|---|---|
| tgagttttga ggttgcttca gtgaacattc aacgctgtcg gtgagtttgg aattaaaatc | 60 |
| aaaaccatcg accgttgatt gtaccctatg gctaaccatc atctactcca | 110 |

<210> SEQ ID NO 64
<211> LENGTH: 110
<212> TYPE: DNA
<213> ORGANISM: Homo sapiens

<400> SEQUENCE: 64

| | |
|---|---|
| cctgtgcaga gattattttt taaaaggtca caatcaacat tcattgctgt cggtgggttg | 60 |
| aactgtgtgg acaagctcac tgaacaatga atgcaactgt ggccccgctt | 110 |

<210> SEQ ID NO 65
<211> LENGTH: 1357
<212> TYPE: DNA
<213> ORGANISM: Homo sapiens

<400> SEQUENCE: 65

| | |
|---|---|
| agaagggcta tcaggccagc cttcagagga ctccaaggaa cattcaacgc tgtcggtgag | 60 |
| tttgggattt gaaaaaacca ctgaccgttg actgtaccct ggggtcctta cagacgacac | 120 |
| tacatttcct gaagcaaaag agcaagctgt accttcacat gtcacatgag ttcaccagaa | 180 |
| atggtcctgc aatcccccaa atgtggtcca gtgaatttta ttcctactgc tcactgttcc | 240 |
| ttgctttctg ttgtgtgttt tattattatt tgtttgtttt tacaaaaaaa gtgtttcatt | 300 |
| tcaacaaggt aaggagcagt ccatgatgat atctaatgta cctacatgtc tcctagatat | 360 |
| gcaccattct ggtgagaaac aggacgtagc aagtaaaaat ttattaaaaa tacgtatttt | 420 |
| gttttggaat aaaatccagt taaataatta ctcccatttc tcccacatcc tctcaaaatt | 480 |
| tttaattagg ggcaagggga ggatttaata agcaaaaata gcacaaaatt atccaattgt | 540 |
| gacagttctt atcacatttc actttgaatt atagttaata tggttaattt ttgatatccc | 600 |
| agttagagca tgagctattg ccttactagt gcccacatat ccccacatat gcttatttaa | 660 |
| atgtttgcta aattcaagca aaaacttagc cctggagtca gtcagatctg ggatgaatct | 720 |
| tggctcaagc ccttaactag ttatttgacc ccctaagcaa gtgtctcagt tttctcacat | 780 |
| ataaaacaga ggctaagagt acctatcatg gagttttgag actcaatgag ataatatata | 840 |
| aggtgctttg taccattact agcccacagc aaatgctcaa tatatgtaag ctgttattat | 900 |
| taaactccaa cataatctgc taatttacct caaaaaagca ctcatacttc tcagttcaaa | 960 |
| acaaagagga aaagcaggtc cctcagctgt ggtttacagg tactaatatg caagcactgc | 1020 |
| ctgtgtggcg cagtgctacc tgtgaggttc tccaagcact ccttccttct ctgaaccaca | 1080 |
| gcttcctcat ctgcaataac ctcccagctc caatgtcaat gttatggaca cctgtgtggg | 1140 |
| ccctcaatca tgcagatggc tggttactaa gggagaagcc agacacacag acttcaaaga | 1200 |
| actgagatga aaagaagag ccaggagtca gccaggagg gcaaaggcaa ccccaccaac | 1260 |
| tgaaaacact gatggctgca ctcaacattc attgctgtcg gtgggtttga gtctgaatca | 1320 |

-continued

```
actcactgat caatgaatgc aaactgcgga ccaaaca                                   1357

<210> SEQ ID NO 66
<211> LENGTH: 110
<212> TYPE: DNA
<213> ORGANISM: Homo sapiens

<400> SEQUENCE: 66
agaagggcta tcaggccagc cttcagagga ctccaaggaa cattcaacgc tgtcggtgag         60
tttgggattt gaaaaaacca ctgaccgttg actgtacctt ggggtcctta                   110

<210> SEQ ID NO 67
<211> LENGTH: 89
<212> TYPE: DNA
<213> ORGANISM: Homo sapiens

<400> SEQUENCE: 67
ctgatggctg cactcaacat tcattgctgt cggtgggttt gagtctgaat caactcactg         60
atcaatgaat gcaaactgcg gaccaaaca                                           89

<210> SEQ ID NO 68
<211> LENGTH: 313
<212> TYPE: DNA
<213> ORGANISM: Homo sapiens

<400> SEQUENCE: 68
cggaaaattt gccaagggtt tgggggaaca ttcaacctgt cggtgagttt gggcagctca         60
ggcaaaccat cgaccgttga gtggaccctg aggcctggaa ttgccatcct cctgccggtg       120
actctgacct tccagatcta gggggcctg gggagccccc aatccagcct ggcacgtcc         180 cctcccctag gccacagccg aggtcacaat caacattcat tgttgtcggt gggttgtgag       240
gactgaggcc agacccaccg ggggatgaat gtcactgtgg ctgggccaga cacggcttaa       300
ggggaatggg gac                                                           313

<210> SEQ ID NO 69
<211> LENGTH: 9
<212> TYPE: PRT
<213> ORGANISM: Artificial Sequence
<220> FEATURE:
<223> OTHER INFORMATION: Synthetic tag polypeptide

<400> SEQUENCE: 69

Tyr Pro Tyr Asp Val Pro Asp Tyr Ala
1               5

<210> SEQ ID NO 70
<211> LENGTH: 4
<212> TYPE: PRT
<213> ORGANISM: Artificial Sequence
<220> FEATURE:
<223> OTHER INFORMATION: Synthesized sequence

<400> SEQUENCE: 70

Pro Pro Gly Lys
1
```

ROLE OF MIRNA IN T CELL LEUKEMIA

FEDERALLY SPONSORED RESEARCH AND DEVELOPMENT

This invention was made with Government support under grant RO1-HL081612 awarded by the National Institutes of Health. The Government has certain rights in this invention.

BACKGROUND OF THE INVENTION

Leukemia is a cancer involving bone marrow, circulating blood cells, and organs such as the spleen and lymph nodes. It is usually characterized by an abnormal proliferation of leukocytes. Leukemias are classified as either acute or chronic based on cellular maturity. Acute leukemias consist of predominantly immature, poorly differentiated cells; chronic leukemias have more mature cells. Acute leukemias are divided into lymphocytic (ALL) and myelocytic (AML) types. Chronic leukemias are described as lymphocytic (CLL) or myelocytic.

ALL is the most common pediatric cancer; it also strikes adults of all ages. Malignant transformation and uncontrolled proliferation of an abnormally differentiated, long-lived hematopoietic progenitor cell result in a replacement of normal marrow by malignant cells, and the potential for leukemic infiltration of the central nervous system and abdominal organs. Symptoms include fatigue, pallor, infection, and easy bruising and bleeding. Examination of peripheral blood smear and bone marrow is usually diagnostic. Treatment typically includes combination chemotherapy to achieve remission, intrathecal chemotherapy for CNS prophylaxis and/or cerebral irradiation for intracerebral leukemic infiltration, consolidation chemotherapy with or without stem cell transplantation, and maintenance chemotherapy for 1 to 3 years to avoid relapse.

Two thirds of all ALL cases occur in children, with a peak incidence at age 2 to 10; ALL is the most common cancer in children and the second most common cause of death in children <age 15. A second rise in incidence occurs with aging after age 45.

The most common type of leukemia in the Western world, CLL involves mature-appearing defective neoplastic lymphocytes with an abnormally long life span. The peripheral blood, bone marrow, spleen, and lymph nodes undergo leukemic infiltration. Symptoms may be absent or may include lymphadenopathy, splenomegaly, hepatomegaly, and non-specific symptoms attributable to anemia (fatigue, malaise). Diagnosis is by examination of peripheral blood smear and bone marrow aspirate. Treatment, delayed until symptoms develop, is aimed at lengthening life and decreasing symptoms and may involve chlorambucil or fludarabine, prednisone, cyclophosphamide, and/or doxorubicin. Monoclonal antibodies, such as alemtuzumab and rituximab, are increasingly being used. Palliative radiation therapy is reserved for patients whose lymphadenopathy or splenomegaly interferes with other organs.

ALL and CLL can each be subdivided into B-cell or T-cell leukemia. In certain cases, the clonal expansion is T cell in type, and even this group has several subtypes (eg, large granular lymphocytes with cytopenias). Chronic leukemic patterns categorized under CLL include prolymphocytic leukemia, leukemic phase of cutaneous T-cell lymphoma (ie, Sézary syndrome), hairy cell leukemia, and lymphoma leukemia (ie, leukemic changes seen in advanced stages of malignant lymphoma). Differentiation of these subtypes from typical CLL is usually straightforward.

As for ALL, a subcategory of ALL is Adult T cell leukemia (ATL), which is usually a highly aggressive non-Hodgkin's lymphoma. T-cell-prolymphocytic leukemia (T-PLL) is a mature T-cell leukemia with aggressive behavior and predilection for blood, bone marrow, lymph nodes, liver, spleen, and skin involvement. T-PLL primarily affects adults over the age of 30. T-cell acute lymphoblastic leukemia (T-ALL) is another type of ALL that mainly affects children and adolescents. This aggressive tumor is linked with a poor prognosis, resulting in rapid fatality in the absence of treatment. Current therapy for T-ALL requires multi-agent combination chemotherapy with long-term survival rate of only 30-40% among patients under 60 years of age.

Signaling pathways has been investigated in the context of T-cell maturation and malignant transformation. Certain genetic mutations found in ALLs highlight the importance of pre-TCR signaling and Notch signaling in leukemias.

The progressive maturation of $\alpha\beta$ T cells in the thymus is a highly ordered process broadly characterized by the expression of CD4 and CD8 co-receptors. Early T cell progenitors are double negative (DN) for both CD4 and CD8, which can be further subdivided based on the unique expressions of CD44 and CD25 in the following order of development: DN1 (CD44+ CD25−), DN2 (CD44+ CD25+), DN3 (CD44− CD25+), and DN4 (CD44− CD25−) (Godfrey et al., 1993). At the DN2 stage, the rearrangement of the T-cell receptor (TCR$\beta$) locus is initiated by recombinase-activating gene 1 (RAG-1) and RAG-2 and proceeds until a functional TCR$\beta$ chain is generated at the DN3 stage (Capone et al., 1998; Godfrey et al., 1994; Livak et al., 1999). In DN3 cells, only the productively rearranged TCR$\beta$ are allowed to pair with invariant pre-T$\alpha$ and CD3 molecules to form a pre-TCR complex, signifying the completion of the first critical checkpoint during T cell development, known as $\beta$-selection (Dudley et al., 1994; Mallick et al., 1993). The ensuing signals from the pre-TCR complex act to promote survival and expansion of DN3 thymocytes, terminate further rearrangement of the TCR$\beta$ locus, and induce differentiation into the DP stage (Michie and Zuniga-Pflucker, 2002; von Boehmer et al., 1999). As early thymic progenitors exit the DN stage, they acquire the expression of both CD4 and CD8 to become double positive (DP) thymocytes and a select few will mature into CD4 or CD8 single positive (SP) cells.

In addition to the autonomous signals received through the pre-TCR, extrinsic signals derived form the thymic microenvironment are also fundamental for the proper development of T cells. In particular, signaling through Notch receptors in common lymphoid progenitors that had colonized the thymus have been reported to influence the T/B cell lineage decision by suppressing B cell development and promoting T cell commitment (Pui et al., 1999; Radtke et al., 1999). Furthermore, $\alpha\beta$-committed progenitors, which are first evident at the DN2 stage, rely on Notch signals for survival signals prior to TCR$\beta$ expression (Ciofani et al., 2006). Following $\beta$-selection, $\alpha\beta$-committed progenitors may continue to depend on Notch signals, which synergize with pre-TCR to induce expansion and differentiation during the DN3 to DP transition (Garbe and von Boehmer, 2007; Guidos, 2006). The importance of Notch activity for T cell commitment and differentiation throughout DN stages was particularly evident as OP9 stromal cell line ectopically expressing the Notch ligand Delta-like 1 (DL1) was shown to support T cell differentiation from hematopoietic progenitors (Schmitt and Zuniga-Pflucker, 2002).

Although Notch and pre-TCR signaling pathways are both involved in T-cell maturation and cell expansion, there is currently no known effective therapy against leukemia that take into account the cooperativity between the two pathways. Methods of regulating multiple pathways relevant in cellular expansion and maturation are of great interest for clinical and research purposes.

Small regulatory RNAs mediate a fundamental layer of gene regulation known as RNA interference. These tiny fragments of nucleic acid can globally affect gene expression, and in turn, alter developmental processes in plants and animals (Ambros, 2003; Bartel, 2004). Among these small non-coding RNAs, microRNAs (miRNAs) represent a family of naturally occurring RNA molecules of ~22 nucleotides in length that mediate posttranscriptional gene repression by binding with imperfect complementarity to the 3' untranslated region (3'UTR) of their cognate target messenger RNA (mRNA), resulting in message degradation or translational repression (Pillai et al., 2007). mRNA genes are abundant in nature and computational prediction suggests that at least one-third of all human protein-coding genes are regulated by miRNAs (Berezikov et al., 2005; Miranda et al., 2006). Their impressions in mammals have also been appreciated as miRNAs were shown to regulate insulin secretion (Poy et al., 2004), adipocyte differentiation (Esau et al., 2004), and heart development (Zhao et al., 2007; Zhao et al., 2005).

Chen et al. (2004) Science 303:83 describe the modulation of hematopoietic lineage differentiation by microRNAs. Krutzfeldt et al. (2005) Nature 438:685 describe the silencing of microRNAs in vivo with antagomirs.

The miR-181a RNA is represented in published US Patent Applications: 20060185027, Systems and methods for identifying miRNA targets and for altering miRNA and target expression; 20060134639, Method for the determination of cellular transcriptional regulation; 20060105360, Diagnosis and treatment of cancers with microRNA located in or near cancer associated chromosomal features; 20060099619, Detection and quantification of miRNA on microarrays; 20060057595, Compositions, methods, and kits for identifying and quantitating small RNA molecules; 20060019286, High throughput methods relating to microRNA expression analysis; 20050261218, Oligomeric compounds and compositions for use in modulation small non-coding RNAs; 20050260648, Method for the determination of cellular transcriptional; 20050256072, Dual functional oligonucleotides for use in repressing mutant gene expression.

SUMMARY OF THE INVENTION

Methods and compositions are provided for treating leukemia. In certain embodiments, the method and composition are formulated to specifically treat leukemia involving T cells by targeting miR-181a/b. In some embodiments, the genetic sequence encoding miR-181a/b, and/or the expression levels of miR-181a/b and its targets are determined in connection with diagnosing T-cell leukemias, where alterations in the sequence or level of expression are correlated with aberrations in the development of T cell and can be used in prognosis to determine the treatment strategy. The discovery that certain microRNAs, including without limitation, miR-181a/b, regulate signaling molecules in more than one pathway, such as both the pre-TCR and the Notch pathway, makes such microRNAs ideal therapeutic targets in treating leukemia. In certain embodiments, the method and composition provided is a therapeutic method that includes downregulating miR-181a/b in combination with other conventional therapy.

In some embodiments of the invention, an inhibitor of mir181a is targeted to the sequence of the primary transcript of mir-181a-1/b-1 and is not targeted to the primary sequence of mir181c/d. Such a selective inhibitor may be targeted to a region of the mir181a/b gene or primary transcript that is other than the mature microRNA, e.g. the loop sequence, sequences flanking the stem, etc.

In other embodiments, by altering the activity or levels of proteins involved in both the Notch signaling pathway and the pre-T-cell receptor (TCR) signaling pathway through miRNA regulation, the development and transformation of T cells may be modulated. Target cells and tissues of interest for modulation include bone marrow, e.g. stem cells, lymphocyte progenitor cells, etc.; thymocytes; peripheral blood, e.g. T helper cells, cytotoxic T cells, memory T cells, regulatory T cells, and the like.

In one embodiment of the invention, miR-181a/b and the targets of miR-181a/b as described herein are used in the screening of candidate agents for modulating both Notch signaling and pre-TCR signaling. Embodiments of interest include screening for agents that either downregulate or upregulate miR-181a/b and its targets.

These and other embodiments of the invention will be apparent from the description that follows. The compositions, methods, and techniques described in this disclosure hold considerable promise for use in diagnostic, drug screening, and therapeutic applications.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 4A-4B Specific silencing of Nrarp by shRNA does not recapitulate miR-181a functional activity. (A) Western blot analyses confirm the efficiencies by which shRNAs can repress Nrarp protein expression. shRNAs are designed to target the coding region (ORF1, 394-412) or sites in the 3'UTR (UTR1, 892-910; UTR2, 971-989) of the Nrarp gene. Cell lysates were extracted from BOSC23 cells co-transfected with HA-tagged Nrarp-FL and shRNAs. Relative Nrarp protein levels were determined by densitometry and normalized to β-actin loading control. (B) Silencing Nrarp protein expression by shRNAs has no apparent effect on DP cell development. Percentage of DP cells among the differentiating thymic progenitors ectopically expressing various shRNAs targeting Nrarp were analyzed following an 8 day OP9-DL1 co-culture. Data are displayed as box plots with the red line representing the median (n=12). Representative analysis of three independent experiments is shown. P values were determined using the Mann-Whitney rank sum test as compared to vector control (*: P<0.0001).

FIGS. 5A-5B miR-181a influences pre-TCR signaling by controlling expression of multiple phosphatases during early T cell development. (A) Phosphatases that negatively regulate pre-TCR signaling contain miR-181a binding sites. To determine the significance of predicted miR-181a binding sites on phosphatase function, miR-181a sensitive (ORF+ 3'UTR) and insensitive (ORF only) were ectopically expressed in thymic progenitors, cultured over OP9-DL1 stromal cells for 8 days, and examined for their effects on DP development. Relative changes in % DP are displayed as box plots. (B) Silencing individual phosphatases through shRNAs has no apparent effect on DP cell development. Percentage of DP cells among the differentiating thymic progenitors ectopically expressing shRNA constructs targeting SHP2, or DUSP5, or DUSP6 were analyzed following an 8 day OP9-DL1 co-culture. Short hairpin RNA against SHP1 is used as a negative control, as miR-181a binding sites are absent in the SHP1 gene. For (A) and (B), data are displayed as a relative change in % DP in the form of box plots with the red line representing the median (n=12). Representative analysis of three independent experiments is shown. P values were determined using the Mann-Whitney rank sum test as compared to vector control (*: P<0.0001).

FIG. 9A-9B Original and modified in vitro system to analyze microRNA function in T cell development. (A) Our original OP9-DL1 co-culture system utilized sorted DN thymocytes for retroviral infection and subsequent culture over stromal cells. (B) The assay was modified to confer T cell development from total thymocytes. The modifications included pretreatment of mice with 5-fluorouracil (5-FU) and an additional wash step at day 1 to remove the more differentiated thymocytes (DP and SP).

FIGS. 10A-10C Expansion and differentiation of total thymocytes require the presence of DN thymocytes on OP9-DL1 stromal cells. (A) Schematic diagram depicting the population of thymocytes initiated in the OP9-DL1 Co-culture assay: unseparated thymocytes (1×10$^5$) or their representative number of DN, DP, CD4SP, CD8SP, and their respective depleted fractions. (B) Thymocyte expansion as displayed by total cell number present in culture following 8 days. OP9-DL1 cells are GRP positive and were excluded from the total cell count based on GFP expression. (C) All populations that contain DN thymocytes were analyzed for their distribution of DN, CD4SP, CD8SP, and DP cells present at termination of culture. Data is presented as absolute percentage (mean±SD, n=12).

FIGS. 13A-13D Putative miR-181a binding sites on Notch signaling molecules and their endogenous expression in thymocyte subpopulations. Murine genes for Numb (A), Numblike (B), Hes6 (C), and LFNG (D) are presented schematically to include the 5'UTR, ORF, and 3'UTR. The approximate locations of the predicted miR-181a pairing site is presented as a bold red line and numbered. Nucleotide numbers that define the 3 regions correspond to their respective GenBank accession number.

FIG. 16 Effects of the mutations in the stem region on mir-181a-1 activity in promoting DP cell development. (A) Scanning mutations in the stem region of the mir-181a-1 gene (SEQ ID NO:1, SEQ ID NO:6-19). Two nucleotides (2-nt mutantsw) or a stretch of nucleotides (segment mutants) in the mature miRNA region are altered. Nucleotides are altered to disrupt their potential base pairing to target genes. Compensatory mutations are also generated on the miR* strand to maintain the secondary structure of the pre-miRNAs. (B) Expression and processing of wild-type mir-181a-1 and stem mutants. Specific probes that perfectly match the mature miR-181a and each of its mutant forms were used in hybridization to determine the expression of mature miR-181a and its stem mutant forms. (C) The effects of mir-181a-1 and its stem mutants on DP cell development. Normalized data from 3-5 independent T cell assays (each with 12 independent replicates, total 36-60 replicates) are pooled and graphed in the distribution box plots to summarize the distribution of the relative activities of mir-181a-1 (shaded grey), the 2-nt mutants, and the segment mutants in DP cell development. Mann-Whitney Rank Sum Tests were performed to determine whether the activities of individual 2-nt mutants were statistically different from those of the control vector (*, p<0.0001) and the mir-181a-1 vector (*, p<0.0001).

FIG. 22 Mir-181a1b1 contributes to maintenance of Notch-induced T-ALL in a mouse model.

DETAILED DESCRIPTION OF THE EMBODIMENTS

Figure 1:
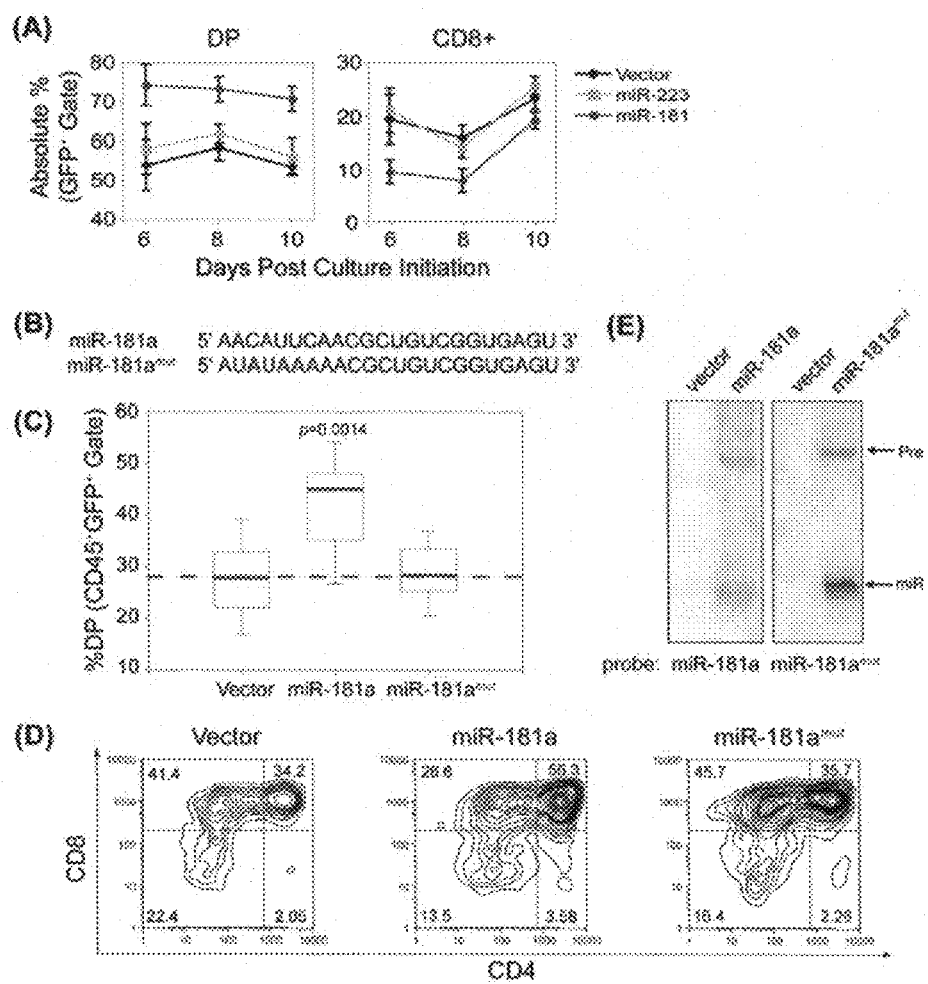
FIGS. 1A-1E miR-181a potentiates DP thymocyte development in OP9-DL1 stromal coculture assay. (A) Sorted DN thymocytes were infected with miRNA-expressing retrovirus (empty vector, miR-181a, miR-223), seeded over OP9-DL1 stromal monolayer, and cultured for 6, 8, and 10 days. FACS analysis was used to determine the absolute % of DP and $CD8^+$ thymocytes remaining in culture among infected thymocytes (n=6, mean±sd). Statistical analysis is presented on supplementary Table I. (B) RNA sequences of mature miR-181a (SEQ ID NO:1) and its mutant form (SEQ ID NO:2). The mutations (red) were introduced in the 'seed' region of miR-181a as defined by the 2nd to 7th nucleotide from the 5' end. (C) 5-FU-primed thymocytes were infected with miRNA-expressing retrovirus and cultured over OP9-DL1 stromal cells for 8 days. FACS analysis was used to determine the percentage of DP thymocytes among infected thymocytes (CD45+GFP+ cells) expressing either no miRNA (vector), miR-181a, or miR-181a$^{mut}$. The absolute % DP from individual cultures (n=12) was converted to a relative change in the % DP by setting functional activities of the empty vector to zero and miR-181 to one. Data are presented as box plots describing the 25th to 75th percentile, while the red line represents the median and the bars define the 5th to 95th percentile. Representative analysis of four independent experiments is shown. P values were determined using the Mann-Whitney rank sum test as compared to vector control. (D) FACS plots displaying the distribution of $CD45^+GFP^+$ thymocytes expressing CD4 and CD8 remaining in culture after 8 days. Representative of twelve independent cultures per experiment; four experiments performed. (E) Mature miRNA expression from the miR-181a and miR-181a$^{mut}$ expression constructs were confirmed by Northern blot analyses using DNA probes against the mature miR-181a and miR-181a$^{mut}$ sequences, respectively.

Methods and compositions are provided for treating leukemia. In certain embodiments, the method and composition are formulated to specifically treat leukemia involving T cells by targeting miR-181a/b. In some embodiments, the genetic sequence encoding miR-181a/b, and/or the expression levels of miR-181a/b and its targets are determined in connection with diagnosing T-cell leukemias, where alterations in the sequence or level of expression are correlated with aberrations in the development of T cell and can be used in prognosis to determine the treatment strategy.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides methods and compositions modulating T cell signaling threshold and T cell sensitivity to antigen. In further describing the subject invention, the subject methods are described first in greater detail, followed by a review of various representative applications in which the subject invention finds use as well as kits that find use in practicing the subject invention.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

MicroRNAs (miRNAs) are an abundant class of non-coding RNAs that are believed to be important in many biological processes through regulation of gene expression. These non-coding RNAs that can play important roles in development by targeting the messages of protein-coding genes for cleavage or repression of productive translation. Humans have between 200 and 255 genes that encode miRNAs, an abundance corresponding to almost 1% of the protein-coding genes.

MicroRNAs of interest for use in the methods of the invention include those natural RNAs expressed in cells of the immune system. For example, see Min and Chen (2006) Methods Mol. Biol. 342:209-27 for methods and strategies for dissecting miRNA function during hematopoietic lineage differentiation. Chowdhury and Novina (2005) Adv Immunol. 88:267-92, describe RNAi and RNA-based regulation of immune system function. Chowdhury and Novina (2005) Immunol Cell Biol. 83(3):201-10 discuss potential roles for short RNAs in lymphocytes. Each of these references is herein specifically incorporated by reference for the teaching of microRNAs expressed in cells of the immune system, and for the specific microRNAs disclosed.

miR-181a has been identified as one of three miRNAs that are specifically expressed in hematopoietic cells, with expression dynamically regulated during early hematopoiesis and lineage commitment. The role of miR-181 in the B-lymphoid cells has been described by Chen et al., supra. miR-181 is very strongly expressed in the thymus, the primary lymphoid organ, which mainly contains T lymphocytes. It is also strongly expressed in the brain and lung and is detectable in bone marrow and the spleen. Mature miR-181 expression has been reported in bone marrow cells and up-regulated in differentiated B lymphocytes, which are marked by the B220 surface antigen.

The nucleotide sequence of representative miR-181a sequences is provided in Table 1. It can be seen that the sequence is very highly conserved among primate and mammalian species.

TABLE 1 miR-181a Sequences

| organism | Genbank accession | DNA sequence | RNA sequence |
|---|---|---|---|
| Bos Taurus | DQ274916 | SEQ ID NO: 45<br>aacattcaacgctgtcggtgag | SEQ ID NO: 46<br>aacauucaacgcugucggugag |
| Macaca nemestrina | AY866169 | SEQ ID NO: 47<br>aacattcaacgctgtcggtgag | SEQ ID NO: 48<br>aacauucaacgcugucggugag |
| Saguinus labiatus | AY866168 | SEQ ID NO: 49<br>aacattcaacgctgtcggtgag | SEQ ID NO: 50<br>aacauucaacgcugucggugag |
| Macaca mulatta | AY866167 | SEQ ID NO: 51<br>aacattcaacgctgtcggtgag | SEQ ID NO: 52<br>aacauucaacgcugucggugag |
| Pan troglodytes | AY866166 | SEQ ID NO: 53<br>aacattcaacgctgtcggtgag | SEQ ID NO: 54<br>aacauucaacgcugucggugag |
| Pan paniscus | AY866165 | SEQ ID NO: 55<br>aacattcaacgctgtcggtgag | SEQ ID NO: 56<br>aacauucaacgcugucggugag |
| Gorilla gorilla | AY866164 | SEQ ID NO: 57<br>aacattcaacgctgtcggtgag | SEQ ID NO: 58<br>aacauucaacgcugucggugag |
| Homo sapiens | | SEQ ID NO: 59<br>aacattcaacgctgtcggtgagt | SEQ ID NO: 60<br>aacauucaacgcugucggugagu |
| Mus musculus | AJ560723 | SEQ ID NO: 61<br>aacattcaacgctgtcggtgagt | SEQ ID NO: 1<br>aacauucaacgcugucggugagu |

As used herein, the term miR-181a may refer to any of the provided sequences, usually in reference to a 22 or 23 nucleotide polynucleotide comprising the sequence aacattcaacgctgtcggtgag. Included in the scope of the term "microRNA" is included synthetic molecules with substantially the same activity as the native microRNA, e.g. synthetic oligonucleotides having altered chemistries, as are known in the art.

In practicing certain embodiments of the subject methods, an effective amount of a miR181a agent is introduced into the target cell to either increase the activity or silence miR181a, where any convenient protocol for introducing the agent into the target cell may be employed. The target cell is usually a cell of the T lymphocyte lineage, including, without limitation, hematopoietic stem cells, committed lymphocyte progenitors, pro-T cells, pre-T cells, thymocytes, mature T cells, and memory T cells. Mature T cells include th1 helper T cells, th2 helper T cells, th3 helper T cells, cytotoxic T cells, natural killer T cells (NKT cells), T regulatory cells, and the like.

The subject methods are used for prophylactic or therapeutic purposes. As used herein, the term "treating" is used to refer to both prevention of disease, and treatment of pre-existing conditions. For example, the prevention of T-cell proliferative diseases may be accomplished by administration of the agent prior to development of overt disease. The treatment of ongoing disease, where the treatment stabilizes or improves the clinical symptoms of the patient, is of particular interest.

As is known in the art, miRNAs are single stranded RNA molecules that range in length from about 20 to about 25 nt, such as from about 21 to about 24 nt, e.g., 22 or 23 nt. The target miR181a may or may not be completely complementary to the introduced miR181a agent. If not completely complementary, the miRNA and its corresponding target viral genome are at least substantially complementary, such that the amount of mismatches present over the length of the miRNA, (ranging from about 20 to about 25 nt) will not exceed about 8 nt, and will in certain embodiments not exceed about 6 or 5 nt, e.g., 4 nt, 3 nt, 2 nt or 1 nt.

The miR181a agent may increase or decrease the levels of miR181a in the targeted cell. Where the agent is an inhibitory agent, it inhibits the activity of the target miRNA by reducing the amount of miR181a RNA present in the targeted cells, where the target cell may be present in vitro or in vivo. By "reducing the amount of" is meant that the level or quantity of the target miRNA in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods.

By miRNA inhibitory agent is meant an agent that inhibits the activity of the target miRNA. The inhibitory agent may inhibit the activity of the target miRNA by a variety of different mechanisms. In certain embodiments, the inhibitory agent is one that binds to the target miRNA and, in doing so, inhibits its activity. Representative miRNA inhibitory agents include, but are not limited to: antisense oligonucleotides, shRNA, and the like. Other agents of interest include, but are not limited to: naturally occurring or synthetic small molecule compounds of interest, which include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing appropriate screening protocols.

In some embodiments, precursors for mature miRNAs (precursor miRNAs), including pre-miRNAs and pri-miRNAs, are employed to provide a more selective range of mRNA targets than are normally obtained with mature miRNAs. The naturally occurring precursor miRNA molecules may be modified for increasing selectivity in binding to target mRNA or synthetic precursor miRNAs prepared differing from the wild-type pre-miRNAs portion in their flanking region, stem and/or loop. Either the stem or loop regions may be modified, where the loop regions are identified as enhancing selectivity for target mRNAs, whereby target mRNAs are determined based on complementarity to both the guiding sequence of the stem and at least 3 nt of the loop. Alternatively, synthetic pre-miRNAs and pri-miRNAs are prepared where the seed sequence and at least 2 nt of the loop are complementary to the target mRNA, desirably without bulges or interruptions between binding nucleotides.

In some embodiments, a target is selected that distinguishes between a mir181a/b sequence and a mir181c/d sequence. In other words, such a target has sufficient complementary to mir181a/b to selectively bind to, and inhibit activity of that microRNA; but will not specifically bind to and inhibit the activity of the mir181c/d microRNAs. The target may be any target sequence within, for example, the human chromosome sequence corresponding to the pri-miR-181a-1/b-1 transcribed sequence, which is human chromosome 1, nt. 197094625-197094905 (−) strand as set forth in the Genbank human genome database:

(SEQ ID NO: 62)
TGAGTTTTGAGGTTGCTTCAGTGAACATTCAACGCTGTCGGTGAGTTTGGAATTAAAATCAAAACCATCG

ACCGTTGATTGTACCCTATGGCTAACCATCATCTACTCCATGGTGCTCAGAATTCGCTGAAGACAGGAAA

CCAAAGGTGGACACACCAGGACTTTCTCTTCCCTGTGCAGAGATTATTTTTTAAAAGGTCACAATCAACA

TTCATTGCTGTCGGTGGGTTGAACTGTGTGGACAAGCTCACTGAACAATGAATGCAACTGTGGCCCCGCT

T

The precursor RNA to mir181a-1 corresponds to nt. 197094905-197094905 of the human genome sequence, and the mir181b-1 precursor sequence corresponds to nt. 197094625-197094734, which are as follows:

(SEQ ID NO: 63)
miR-181a-1
TGAGTTTTGAGGTTGCTTCAGTGAACATTCAACGCTGTCGGTGAGTTTGGAATTAAAATCAAAACCATCG

ACCGTTGATTGTACCCTATGGCTAACCATCATCTACTCCA where the non-mature microRNA nucleotides start at reside 46

(SEQ ID NO: 64)
miR-181b-1
CCTGTGCAGAGATTATTTTTTAAAAGGTCACAATCAACATTCATTGCTGTCGGTGGGTTGAACTGTGTGG

ACAAGCTCACTGAACAATGAATGCAACTGTGGCCCCGCTT where the non-mature microRNA starts at residue 58.

Alternatively the target may be any target sequence within, for example, the human chromosome sequence corresponding to the pri-miR-181a-2/b-2 transcribed sequence, which is human chromosome 9, nt. 126494542-126495898 (+) strand as set forth in the Genbank human genome database:

(SEQ ID NO: 37)
AGAAGGGCTATCAGGCCAGCCTTCAGAGGACTCCAAGGAACATTCAACGCTGTCGGTGAGTTTGGGATTT

GAAAAAACCACTGACCGTTGACTGTACCTTGGGGTCCTTACAGACGACACTACATTTCCTGAAGCAAAAG

AGCAAGCTGTACCTTCACATGTCACATGAGTTCACCAGAAATGGTCCTGCAATCCCCCAAATGTGGTCCA

GTGAATTTTATTCCTACTGCTCACTGTTCCTTGCTTTCTGTTGTGTGTTTTATTATTATTTGTTTGTTTT

TACAAAAAAAGTGTTTCATTTCAACAAGGTAAGGAGCAGTCCATGATGATATCTAATGTACCTACATGTC

TCCTAGATATGCACCATTCTGGTGAGAAACAGGACGTAGCAAGTAAAAATTTATTAAAAATACGTATTTT

GTTTTGGAATAAAATCCAGTTAAATAATTACTCCCATTTCTCCCACATCCTCTCAAAATTTTTAATTAGG

GGCAAGGGGAGGATTTAATAAGCAAAAATAGCACAAAATTATCCAATTGTGACAGTTCTTATCACATTTC

-continued

```
ACTTTGAATTATAGTTAATATGGTTAATTTTTGATATCCCAGTTAGAGCATGAGCTATTGCCTTACTAGT

GCCCACATATCCCCACATATGCTTATTTAAATGTTTGCTAAATTCAAGCAAAAACTTAGCCCTGGAGTCA

GTCAGATCTGGGATGAATCTTGGCTCAAGCCCTTAACTAGTTATTTGACCCCCTAAGCAAGTGTCTCAGT

TTTCTCACATATAAAACAGAGGCTAAGAGTACCTATCATGGAGTTTTGAGACTCAATGAGATAATATATA

AGGTGCTTTGTACCATTACTAGCCCACAGCAAATGCTCAATATATGTAAGCTGTTATTATTAAACTCCAA

CATAATCTGCTAATTTACCTCAAAAAAGCACTCATACTTCTCAGTTCAAAACAAAGAGGAAAAGCAGGTC

CCTCAGCTGTGGTTTACAGGTACTAATATGCAAGCACTGCCTGTGTGGCGCAGTGCTACCTGTGAGGTTC

TCCAAGCACTCCTTCCTTCTCTGAACCACAGCTTCCTCATCTGCAATAACCTCCCAGCTCCAATGTCAAT

GTTATGGACACCTGTGTGGGCCCTCAATCATGCAGATGGCTGGTTACTAAGGGAGAAGCCAGACACACAG

ACTTCAAAGAACTGAGATGGAAAAGAAGAGCCAGGAGTCAGCCAGGGAGGGCAAAGGCAACCCCACCAAC

TGAAAACACTGATGGCTGCACTCAACATTCATTGCTGTCGGTGGGTTTGAGTCTGAATCAACTCACTGAT

CAATGAATGCAAACTGCGGACCAAACA
```

The precursor RNA to mir181a-2 corresponds to chr. 9, nt. 126494542-126494651 of the human genome sequence, and the mir181b-2 precursor sequence corresponds to chr. 9, nt. 126495810-126495898, which are as follows:

```
                                                              (SEQ ID NO: 66)
miR-181a-2
AGAAGGGCTATCAGGCCAGCCTTCAGAGGACTCCAAGGAACATTCAACGCTGTCGGTGAGTTTGGGATTT

GAAAAAACCACTGACCGTTGACTGTACCTTGGGGTCCTTA
``` where the non-mature microRNA nucleotides start at reside 61.

```
                                                              (SEQ ID NO: 67)
miR-181b-2
CTGATGGCTGCACTCAACATTCATTGCTGTCGGTGGGTTTGAGTCTGAATCAACTCACTGATCAATGAAT

GCAAACTGCGGACCAAACA
``` where the non-mature microRNA starts at residue 37.

In one embodiment of the invention, the target sequence is a sequence that does not specifically bind to pri-miR-181c/d transcribed sequence, which is human chromosome 19, nt. 13846513-13846825 as set forth in the Genbank human genome database and reproduced below. Polynucleotide targets of interest comprise at least about 12 nt, at least about 15 nt, at least about 18 nt, at least about 20 nt, at least about 23 nt of sequence identity to a contiguous sequence set forth in SEQ ID NO:34 or SEQ ID NO:37, or the subset sequences of SEQ ID NO:35, 36, 38 and 39 which target comprises less than about 15 contiguous nucleotides, usually less than about 12 contiguous nt. of sequence identity to a contiguous sequence set forth in SEQ ID NO:40.

In developing algorithms for determining target mRNAs, the algorithms may include complementarity to at least a sequence of 2 nt, at least 4 nt, at least 6 nt, at least 8 nt, at least 10 nt, at least 12 nt, at least 15 nt, at least 18 nt, at least 20 nt of the loop sequence. Precursor miRNAs are screened for their binding profile of mRNAs in a mixture of mRNAs in vitro and in vivo and specific targets are identified by complementarity and specificity. Precursor miRNAs may be produced based on known pre-miRNAs and pri-miRNAs or on mRNA sequences, where specificity is enhanced by increasing complementarity of at least some of the nucleotides in the loop. Precursor miRNAs with improved target gene selectivity and/or modified activity may be selected from a library of precursor miRNAs molecules with randomized loop sequences through vitro and in vivo screening assay. Enhanced specificity in translational suppression is achieved with the subject precursor miRNAs and mimetics thereof, which may be provided by introduction into cells as a composition or introduced into cells as DNA for transcription of the precursor miRNAs. The subject precursor miRNAs may

```
                                                              (SEQ ID NO: 68)
CGGAAAATTTGCCAAGGGTTTGGGGGAACATTCAACCTGTCGGTGAGTTTGGGCAGCTCAGGCAAACCAT

CGACCGTTGAGTGGACCCTGAGGCCTGGAATTGCCATCCTCCTGCCGGTGACTCTGACCTTCCAGATCTA

GGGGGGCCTGGGGAGCCCCCAATCCAGCCTGGGCACGTCCCCTCCCCTAGGCCACAGCCGAGGTCACAAT

CAACATTCATTGTTGTCGGTGGGTTGTGAGGACTGAGGCCAGACCCACCGGGGGATGAATGTCACTGTGG

CTGGGCCAGACACGGCTTAAGGGGAATGGGGAC.
``` be used in arrays, where at least two precursor miRNAs, as may be modified, will have similar sequences, but stems and/or loops differing by at least one nucleotide. Precursor miRNAs with unique loop nucleotides are screened for antisense oligonucleotides that complement to the loop region of the precursor miRNAs that can selectively silence miRNA genes which encode identical or nearly identical mature miRNAs. The precursor miRNAs molecules may be redesigned to recognize novel sequences for repression. Either or both the stem or loop regions may be designed, where the loop regions are identified as enhancing selectivity for target mRNAs, whereby target mRNAs are determined based on complementarity to both the guiding sequence of the stem and at least 3 nt of the loop. Target mRNAs may be perfectly matched or be partly complementary to the guiding sequence of the stem and at least 3 nt of the loop. Synthetic or DNA encoded re-designed precursor miRNAs are prepared where the seed sequence and at least 2 nt of the loop are complementary to the target mRNA, desirably without bulges or interruptions between binding nucleotides.

For example, miR181a activity may be modulated by introducing into a target cell a mutated precursor miRNA, where the precursor miRNA comprises a stem sequence and a loop sequence, the stem sequence comprising a seed sequence wherein the seed sequence is substantially complementary to a sequence present in a target mRNA produced in the cell, the loop is mutated by substitution of at least one nucleotide to provide at least 4 nucleotides complementary to nucleotides in said mRNA, where the closest nucleotide in the mRNA sequence complementary to a nucleotide in said loop is from about 16 to 20 nucleotides from said mRNA sequence complementary to said seed sequence; wherein the phenotype of the cell is modulated by the suppression of translation of the mRNA by the mutated precursor miRNA.

In other embodiments, an antisense reagent is an antisense oligonucleotide (ODN), particularly synthetic ODN having chemical modifications from native nucleic acids, or nucleic acid constructs that express such antisense molecules as RNA. The antisense sequence is complementary to the targeted miRNA, and inhibits its expression. One or a combination of antisense molecules may be administered, where a combination may comprise multiple different sequences.

Antisense molecules may be produced by expression of all or a part of the target miRNA sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Anti-sense molecules of interest include antagomir RNAs, e.g. as described by Krutzfeldt et al., supra., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing miRNAs in vivo, chemically modified, cholesterol-conjugated single-stranded RNA analogues complementary to miRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. In representative embodiments, the RNAi agent targets the precursor molecule of the microRNA, known as pre-microRNA molecule. By RNAi agent is meant an agent that modulates expression of microRNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enables one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Where it is desirable to decrease miR-181a/b expression in a cell, an agent may be antisense RNA oligonucleotides, including any of the modified oligonucleotides described above with respect to antisense, e.g. cholesterol conjugates, phosphorothioates linkages, and the like. Alternatively, a vector that expresses such antisense oligonucleotides may also be used.

Expression vectors may be used to introduce the target gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The expression cassette will generally employ an exogenous transcriptional initiation region, i.e. a promoter other than the promoter which is associated with the T cell receptor in the normally occurring chromosome. The promoter is functional in host cells, particularly host cells targeted by the cassette. The promoter may be introduced by recombinant methods in vitro, or as the result of homologous integration of the sequence by a suitable host cell. The promoter is operably linked to the coding sequence of the autoantigen to produce a translatable mRNA transcript. Expression vectors conveniently will have restriction sites located near the promoter sequence to facilitate the insertion of autoantigen sequences.

Expression cassettes are prepared comprising a transcription initiation region, which may be constitutive or inducible, the gene encoding the autoantigen sequence, and a transcriptional termination region. The expression cassettes may be introduced into a variety of vectors. Promoters of interest may be inducible or constitutive, usually constitutive, and will provide for high levels of transcription in the vaccine recipient cells. The promoter may be active only in the recipient cell type, or may be broadly active in many different cell types. Many strong promoters for mammalian cells are known in the art, including the .beta.-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region is provided 3' to the coding region, where the termination region may be naturally associated with the variable region domain or may be derived from a different source. A wide variety of termination regions may be employed without adversely affecting expression.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

As indicated above, the miRNA agent can be introduced into the target cell(s) using any convenient protocol, where the protocol will vary depending on whether the target cells are in vitro or in vivo. A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

For example, the inhibitory agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications.

When liposomes are utilized, substrates that bind to a cell-surface membrane protein associated with endocytosis can be attached to the liposome to target the liposome to T cells and to facilitate uptake. Examples of proteins that can be attached include capsid proteins or fragments thereof that bind to T cells, antibodies that specifically bind to cell-surface proteins on T cells that undergo internalization in cycling and proteins that target intracellular localizations within T cells. Gene marking and gene therapy protocols are reviewed by Anderson et al. (1992) Science 256:808-813.

In some embodiments the inhibitory agent is targeted to the cells of interest through a specific binding moiety. Targets of interest on the surface of T cell leukemias include, without limitation, CD3, CD4, CD8, CD44 and CD25. Particular specificity may be obtained with a bispecific ligand targeted to CD4 and CD8. A targeting complex of particular interest for delivery of nucleotide based reagents, e.g. anti-sense oligonucleotides, siRNA, etc., comprises an antibody-protamine fusion protein, which when mixed with an oligonucleotide, binds the oligonucleotide and selectively delivers the oligonucleotide into cells expressing an antigen recognized by the antibody, resulting in inhibition of miRNA only in those cells that express the antigen. In one embodiment, the binding moiety is a protein or the nucleic acid binding domain of a protein, and the binding moiety is fused to the carboxy portion of the targeting moiety. The location of the targeting moiety may be either in the carboxyl-terminal or amino-terminal end of the construct or in the middle of the fusion protein. Alternatively, the fusion protein may comprise more than one siRNA binding moieties and one or more targeting moieties.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

Depending on the nature of the agent, the active agent(s) may be administered to the host using any convenient means capable of resulting in the desired modulation of miR-181a/b in the target cell. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

The above described methods work in any mammalian cell, where representative mammal cells of interest include, but are not limited to cells of: ungulates or hoofed animals, e.g., cattle, goats, pigs, sheep, etc.; rodents, e.g., hamsters, mice, rats, etc.; lagomorphs, e.g., rabbits; primates, e.g., monkeys, baboons, humans, etc.; and the like.

T cells may be isolated from patient peripheral blood, lymph nodes, or preferably from the site inflammation. Reactivity assays may be performed on primary T cells, or the cells may be fused to generate hybridomas. Such reactive T cells may also be used for further analysis of disease progression, by monitoring their in situ location, T cell receptor utilization, etc. Assays for monitoring T cell responsiveness are known in the art, and include proliferation assays and cytokine release assays.

Proliferation assays measure the level of T cell proliferation in response to a specific antigen, and are widely used in the art. In an exemplary assay, patient lymph node, blood or spleen cells are obtained. A suspension of from about $10^4$ to $10^7$ cells, usually from about $10^5$ to $10^6$ cells is prepared and washed, then cultured in the presence of a control antigen, and test antigens. The test antigens may be any peptides of interest. The cells are usually cultured for several days. Antigen-induced proliferation is assessed by the monitoring the synthesis of DNA by the cultures, e.g. incorporation of $^3$H-thymidine during the last 18H of culture.

Enzyme linked immunosorbent assay (ELISA) assays are used to determine the cytokine profile of reactive T cells, and may be used to monitor for the expression of such cytokines as IL-2, IL-4, IL-5, γIFN, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

The peptides may be defined by screening with a panel of peptides derived from the test protein. The peptides will have at least about 8 and not more than about 30 amino acids, more usually not more than about 20 amino acids in length. A panel of peptides may represent the length of a protein sequence, i.e. all residues are present in at least one peptide.

Diagnostic and Prognostic Methods

In another embodiment of the invention, the detection of changes in miR-181a/b sequence, including changes in the promoter region, and the like, or expression of miR-181a/b is used as a marker in diagnostic or prognostic evaluation of a patient for conditions associated with T cell function, which conditions include, without limitation, chronic or acute leukemia. Diagnostic methods include detection of specific markers correlated with specific stages in the pathological processes leading to conditions associated with T cell mediated leukemia.

In general, such methods involve detecting altered levels or activity of miR-181a/b in the cells or tissue of an individual or a sample therefrom. A variety of different assays can be utilized to detect changes in expression, including both methods that detect the microRNA, the unprocessed transcripts, and evaluation of genomic sequences. In certain embodiments, the methods also involve detecting altered levels of messenger RNA transcripts that contain in its 3' untranslated region (3' UTR) binding sites for miR-181a/b. The quantity and activities of the proteins encoded by these messenger RNA transcripts may also be monitored for diagnosis and prognosis. In certain embodiments, proteins whose messenger RNA transcripts contain binding sites for miR-181a/b in the 3'UTR may include Nrarp, SHP2, DUSP5, DUSP6, and PTPN22.

More specifically, the diagnostic and prognostic methods disclosed herein involve obtaining a sample from an individual and determining qualitatively or quantitatively, the level or activity of miR-181a/b or its targets in the sample. Usually this determined value or test value is compared against some type of reference or baseline value. For example, a sequence that differs from the wild-type miR-181a/b sequence is a marker, as is altered expression levels relative to the wild-type.

Nucleic acids that are specific for the sequence of miR-181a/b are used to screen patient samples for altered activity of the microRNA, or for the presence of altered DNA in the cell. Samples can be obtained from a variety of sources. For example, since the methods are designed primarily to diagnosis and assess risk factors for humans to T cell leukemia, samples are typically obtained from a human subject. However, the methods can also be utilized with samples obtained from various other mammals, such as primates, e.g. apes and chimpanzees, mice, cats, rats, and other animals. Such samples are referred to as a patient sample.

Samples can be obtained from the tissues or fluids of an individual, as well as from cell cultures or tissue homogenates. For example, samples can be obtained from peripheral blood, serum, semen, saliva, tears, urine, fecal material, etc., preferably a hematopoietic cell sample. Also included in the term are derivatives and fractions of such cells and fluids. Samples can also be derived from in vitro cell cultures, including the growth medium, recombinant cells and cell components. The number of cells in a sample will often be at least about $10^2$, usually at least $10^3$, and may be about $10^4$ or more. The cells may be dissociated, in the case of solid tissues, or tissue sections may be analyzed. Alternatively a lysate of the cells may be prepared.

The various test values determined for a sample from an individual believed to have leukemia typically are compared against a baseline value to assess the extent of altered activity or expression, if any. This baseline value can be any of a number of different values. In some instances, the baseline value is a value established in a trial using a healthy cell or tissue sample that is run in parallel with the test sample. Alternatively, the baseline value can be a statistical value (e.g., a mean or average) established from a population of control cells or individuals. For example, the baseline value can be a value or range which is characteristic of a control individual or control population. For instance, the baseline value can be a statistical value or range that is reflective of expression levels for the general population, or more specifically, healthy individuals not susceptible to T cell leukemia. Samples may also be assessed for expression of T cell markers, e.g. CD4, CD8, etc. as known in the art.

Some of the diagnostic and prognostic methods that involve the detection of miR-181a/b or its targets begin with the lysis of cells and subsequent purification of nucleic acids from other cellular material, particularly RNA transcripts. A nucleic acid derived from an RNA transcript refers to a nucleic acid for whose synthesis the RNA transcript, or a subsequence thereof, has ultimately served as a template. Thus, a cDNA reverse transcribed from an RNA, an RNA transcribed from that cDNA, a DNA amplified from the cDNA, an RNA transcribed from the amplified DNA, are all derived from the RNA transcript and detection of such derived products is indicative of the presence and/or abundance of the original transcript in a sample. Thus, suitable samples include, but are not limited to, RNA transcripts, cDNA reverse transcribed from the RNA, cRNA transcribed from the cDNA, DNA amplified from nucleic acids, and RNA transcribed from amplified DNA.

A number of methods are available for analyzing nucleic acids for the presence of a specific sequence, e.g. upregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes for an ischemia associated gene or ischemia pathway gene is then contacted with the cells and the probes allowed to hybridize with neuroprotective gene nucleic acids. Excess probe is digested, washed away and the amount of hybridized probe measured. This approach is described in greater detail by Harris, D. W. (1996) Anal. Biochem. 243:249-256; Singer, et al. (1986) Biotechniques 4:230-250; Haase et al. (1984) Methods in Virology, vol. VII, pp. 189-226; and Nucleic Acid Hybridization: A Practical Approach (Hames, et al., eds., 1987).

A variety of so-called "real time amplification" methods or "real time quantitative PCR" methods can also be utilized to determine the quantity of ischemia associated gene or ischemia pathway gene mRNA present in a sample. Such methods involve measuring the amount of amplification product formed during an amplification process. Fluorogenic nuclease assays are one specific example of a real time quantitation method that can be used to detect and quantitate miR-181a/b. In general such assays continuously measure PCR product accumulation using a dual-labeled fluorogenic oligonucleotide probe—an approach frequently referred to in the literature simply as the "TaqMan" method.

The probe used in such assays is typically a short (ca. 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. For measuring miR-181a/b, the probe is designed to have at least substantial sequence complementarity with a probe binding site on the miR-181a/b transcript. Upstream and downstream PCR primers that bind to regions that flank the miR-181a/b gene may also added to the reaction mixture. Probes may also be made by in vitro transcription methods.

When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter dye from the polynucleotide-quencher complex and resulting in an increase of reporter emission intensity that can be measured by an appropriate detection system.

Compound Screening

Compound screening may be performed using an in vitro model, leukemia cells, a genetically altered cell or animal, purified microRNA, purified protein corresponding to polypeptides demonstrated herein to be regulated by miR-181a/b, and the like. One can identify ligands or substrates that bind to, modulate, inhibit, potentiate, or mimic the action of the microRNA. Assays may include an analysis of T cell expansion and maturation into double positive cells, e.g. as provided in the Examples, where expression of certain receptors, etc. is monitored in a T cell in the absence or presence of a candidate agent. Other assays include analysis of expression of proteins identified herein as being regulated by miR-181a/b. Assays may also include analysis of the specific phosphatase proteins for enzymatic activity, to the effect of the microRNA on phosphatase expression, etc.

In one embodiment, compound screening is performed to determine the activity of a candidate agent with respect to upregulating the activity of negative regulators of one or more signaling pathways involved in T cell maturation and expansion. In certain cases, the signaling pathways include the pre-T cell receptor (TCR) signaling pathway and Notch signaling pathway. Exemplary suppressors of these signaling pathways may include Nrarp, PTPN22 (PTP-PEST), SHP2, and the dual specificity phosphatases DUSP5 and DUSP6 (PYST1). Effective compounds may modulate the cooperativity between proteins involved in different signaling pathways. In certain cases, an effective candidate agent is one that can silence miR-181a/b. In such a screening assay, for example, a candidate agent may also be tested for coordinate up-regulation of the activity of Nrarp, PTPN22, SHP2, DUSP5 and DUSP6. Such an agent may be tested by contacting the purified proteins with a candidate agent, e.g. a phosphatase activator with specificity broad enough to activate at least partially each of these enzymes, and testing the activity of the phosphatase in a suitable assay, e.g. against known substrates. For example, see Kovanen et al. (2003) J Biol. Chem. 278(7):5205-13; Dowd et al. (1998) J Cell Sci. 111 (Pt 22):3389-99; Matthews et al. (1992) Mol Cell Biol. 12(5): 2396-405, each herein specifically incorporated by reference for teachings of assays relevant to the specific phosphatases.

Alternatively, a cell may be contacted with a candidate agent for regulation of transcription or translation of each of these enzymes. In such assays, the miR-181a/b may serve as a negative control for coordinately regulating expression of these proteins.

The microRNA, Notch-signaling suppressors, or phosphatase polypeptides include those that, by virtue of the degeneracy of the genetic code, are not identical in sequence to the disclosed nucleic acids, and variants thereof. Variant sequences can include amino acid (aa) or nucleotide substitutions, additions or deletions. The substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or, where the polypeptide is a member of a protein family, a region associated with a consensus sequence). Variants also include fragments of the polypeptides disclosed herein, particularly biologically active fragments and/or fragments corresponding to functional domains. Fragments of interest will typically be at least about 10 to at least about 15 residues in length, usually at least about 50 residues in length, and can be as long as 300 residues in length or longer, but will usually not exceed about 500 residues in length.

Transgenic animals or cells derived therefrom are also used in compound screening. Transgenic animals may be made through homologous recombination, where the normal locus corresponding to a genetic sequence identified herein is altered. Alternatively, a nucleic acid construct is randomly integrated into the genome. Vectors for stable integration include plasmids, retroviruses and other animal viruses, YACs, and the like. A series of small deletions and/or substitutions may be made in the coding sequence to determine the role of different exons in kinase activity, oncogenesis, signal transduction, etc. Of interest is the use of downregulating miR-181a/b to treat transgenic animal models of leukemia. In these leukemia animal models, expression of the regulated polypeptides in one or more pathways (e.g. Notch1 signaling and pre-TCR signaling) may be altered. Specific constructs of interest include antisense sequences that block expression of the targeted gene and expression of dominant negative mutations. A detectable marker, such as lac Z may be introduced into the locus of interest, where up-regulation of expression will result in an easily detected change in phenotype. One may also provide for expression of the target gene or variants thereof in cells or tissues where it is not normally expressed or at abnormal times of development. By providing expression of the target protein in cells in which it is not normally produced, one can induce changes in cell behavior.

Compound screening identifies agents that coordinately modulate activities of a plurality of microRNAs, each of which may regulate one, two, three, or more signaling pathways. In certain embodiments, the agents target miR-181a/b or miR-181a/b-regulated polypeptides. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. Knowledge of the 3-dimensional structure of the encoded protein, derived from crystallization of purified recombinant protein, could lead to the rational design of small drugs that specifically inhibit activity. These drugs may be directed at specific domains.

The term "agent" as used herein describes any molecule, e.g. protein or pharmaceutical, with the capability of altering or mimicking the physiological function of a ischemia associated kinase corresponding to Ischemia associated genes. Generally a plurality of assay mixtures is run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to miR-181a/b, or decrease the expression of miR-181a/b. Compounds effective in modulating miR-181a/b or one or more other microRNAs are also assayed for their effect on polypeptides that suppress the pre-TCR signaling pathway and/or Notch-signaling pathway, e.g. Nrarp, SHP2, PTN22, DUSP5 and DUSP6. The binding assays usually involve contacting a protein with one or more test compounds and allowing sufficient time for the microRNA and test compounds to form a binding complex. Any binding complexes formed can be detected using any of a number of established analytical techniques. In the case of protein binding assays, methods may include, but are not limited to, co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. The proteins utilized in such assays can be naturally expressed, cloned or synthesized.

Certain screening methods involve screening for a compound that modulates the expression of polypeptides in the TCR signaling pathway, e.g. PTN22, DUSP5 and DUSP6, usually coordinately modulates expression. Such methods generally involve conducting cell-based assays in which test compounds are contacted with one or more cells expressing polypeptides in the TCR signaling pathway, e.g. PTN22, DUSP5 and DUSP6 and then detecting and an increase in polypeptides in the TCR signaling pathway. Some assays are performed with cells of the immune system, e.g. T cells.

Expression can be detected in a number of different ways. The expression level of a gene in a cell can be determined by probing the microRNA or mRNA expressed in a cell with a probe that specifically hybridizes with a transcript (or complementary nucleic acid derived therefrom) of the gene. Probing can be conducted by lysing the cells and conducting Northern blots or without lysing the cells using in situ-hybridization techniques. Alternatively, a protein can be detected using immunological methods in which a cell lysate is probe with antibodies that specifically bind to the protein.

Other cell-based assays are reporter assays. Certain of these assays are conducted with a heterologous nucleic acid construct that includes a promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) Nature 282:864-869), luciferase, β-galactosidase and alkaline phosphatase (Toh, et al. (1980) Eur. J. Biochem. 182:231-238; and Hall et al. (1983) J. Mol. Appl. Gen. 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of a control population (e.g., healthy individuals). Expression levels can also be determined for cells that do not express one of the signaling pathway genes as a negative control. Such cells generally are otherwise substantially genetically the same as the test cells.

A variety of different types of cells can be utilized in the reporter assays. Certain cells are T cells. Other eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal that serves as a model for humans and then determining if the T cell signaling pathway has been altered. The animal models utilized in validation studies generally are mammals. Specific examples of suitable animals include, but are not limited to, primates, mice, and rats.

Certain methods are designed to test not only the ability of a lead compound to alter activity in an animal model, but to provide protection against leukemia. In such methods, a lead compound is administered to the model animal (i.e., an animal, typically a mammal, other than a human). The animal is subsequently subjected to a carcinogen or cancerous mutations, for example. Compounds able to achieve the desired effect are good candidates for further study.

Active test agents identified by the screening methods described herein can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Treatment Methods

The invention further provides methods for reducing growth of cancer cells, particularly T cell leukemias, and in some embodiments, acute T cell leukemia, T-ALL. The method provides for decreasing the number of cancer cells in leukemia, as provided herein, by altering the level of miRNA expression, or increasing the level of and/or increasing an activity of polypeptides associated with suppressing a plurality of pathways involved in T-cell maturation and expansion. In certain embodiments, the altered level of miRNA expression increases the activity or quantity of suppressors of both the Notch signaling and the pre-TCR signaling. In certain cases, decreasing expression or activity of miR-181a/b may increase the inhibition of multiple signaling pathways, leading to inhibition of T cell expansion and transformation.

The method further includes introducing polynucleotides or polypeptides that would result in the effect of decreasing cancer growth. For example, a genetic construct encoding an antisense oligonucleotide, or 'antagomir' of the miRNA sequences set forth in Table 1 can be introduced into cells to silence the target miRNA level in the cell.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with BCSC, etc.

The present invention provides methods for treating cancer, generally comprising administering to an individual in need thereof a substance that reduces cancer cell growth, in an amount sufficient to reduce cancer cell growth and treat the cancer. Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

The present invention also provides a composition for treating cancer. A substance, e.g. a chemotherapeutic drug that reduces cancer cell growth, can be targeted to a cancer cell. Thus, in some embodiments, the invention provides a method of delivering a drug to a cancer cell, comprising administering a complex of drug-polypeptide or drug-polynucleotide to a subject, wherein the complex is specific for one or more miRNA-regulated polypeptides or the miRNA itself, and the drug is one that reduces cancer cell growth, a variety of which are known in the art and discussed above. Targeting may be accomplished by coupling (e.g., linking, directly or via a linker molecule, either covalently or non-covalently, so as to form a drug-antibody complex) a drug to an antibody specific for a miRNA or one or more polypeptides regulated by the miRNA. Methods of coupling a drug to form a complex are well known in the art and need not be elaborated upon herein. Treatment may be provided in combination with other conventional therapy for leukemia.

EXPERIMENTAL

One of the key features of a functioning immune system is its ability to distinguish antigens of foreign origin from those derived endogenously and to mount an immune response against the former. With respect to T cells, this goal is achieved through antigen recognition by T cell receptors (TCRs) and a highly ordered developmental process in the thymus and in secondary lymphoid organs. TCRs constantly sample a diverse set of self and foreign peptide antigens presented in major histocompatibility complexes (MHCs) on the surface of antigen presenting cells (APCs) and these interactions elicit discrete intracellular signals and T cell responses.

Cooperative signaling between the Notch and pre-TCR pathways is required for αβ T cell development but the molecular basis that govern synergy remain elusive. Recent studies suggest that miRNA-mediated gene regulation may represent a fundamental layer of posttranscriptional genetic programs in metazoan genomes and have broad effects on gene expression. miRNA genes are an integral component of animal genomes and are dynamically regulated during development. These ~22-nt RNAs can repress the expression of protein-coding genes by targeting cognate messenger RNAs for degradation or translational repression. The cellular protein machineries involved in miRNA processing and function were also shown to play important functional roles, for example in the development of limbs and T cells in mice.

Furthermore, many miRNAs are differentially regulated in hematopoietic lineages and some have been shown to play roles in controlling the development of immune cells. The mechanisms by which miRNAs exert these effects are unclear, as is whether they have any specific role in the adaptive immune response.

Example 1

The high prevalence of activating mutations in the Notch1 gene among T-ALL patients has sparked much interest to inhibit Notch signaling as a therapeutic modality. However, other signaling pathways, such as pre-TCR signaling, are required for the full penetrance of T-ALL. Given the ability of miR-181a to support active signaling between Notch and pre-TCR pathways by coordinately dampening negative regulators of these pathways, miR-181a represents an ideal therapeutic target for T-ALL. An established mouse model for T-ALL is used to address the importance of miR-181a in disease etiology and demonstrate down-modulation of miR-181a levels as a therapeutic option for T-ALL.

It has been demonstrated that by rendering bone marrow cells Notch ligand-independent through the constitutive expression of the intracellular domain of Notch (ICN), these cells can induce T cell leukemia when adoptively transferred to a lethally irradiated recipient. Within two weeks following bone marrow transplantation (BMT), the recipient mice begin to show signs of T cell leukemia as indicated by the abnormal circulation of immature $CD4^+CD8^+$ double positive (DP) thymocytes. Eventually, all animals receiving the ICN-expressing BM cells will succumb to the disease within 15 weeks post-BMT.

To address the question of whether miR-181a is necessary for the initiation of T-ALL, a conditional knock-out mice for the mir-181a-1/b-1 allele is used. Although miR-181a can be expressed from two genomic loci, preliminary data has shown that deletion of this allele is sufficient to inhibit early T cell development when Cre recombinase-expressing thymic progenitors were cultured over OP9-DL1 stromal cells. As such, thymic progenitors are infected with retrovirus co-expressing Cre recombinase to delete the mir-181a-1/b-1 allele and ICN to induce T cell leukemia. These cells are adoptively transferred to an irradiated recipient and monitored for the development of T cell leukemia. We chose to use T cell lineage committed thymic progenitors rather than pluripotent bone marrow cells for this experiment because it is still unknown how deletion of mir-181a-1/b-1 allele would affect hematopoietic lineage development. It is possible that the absence of miR-181a would divert bone marrow cells away from the T cell lineage, and therefore, would result in a false positive reading if we do not expect to observe circulating immature thymocytes in the periphery blood system. Furthermore, it was revealed that a more aggressive T cell leukemia ensues when immature T cells are used for the adoptive transplantation. By simultaneously deleting the mir-181a-1/b-1 allele and ectopically expressing ICN, it is predicted that T cell leukemia would not develop, largely due to unrepressed Notch negative regulators (i.e., Nrarp) countering the activity of ICN.

To determine if down-modulation of miR-181a levels rescue animals once T-ALL is established, an inducible Cre recombinase system is used. The conditional KO mice are crossed with Cre-ER, which is a fusion protein of Cre with a mutated form of the estrogen receptor. This CreER recombinase is inactive and can only be activated by synthetic estrogen receptor ligand, known as tamoxifen, thereby allowing for external temporal control of Cre activity. The mir-181a-1/b-1$^{flox/flox}$:CreER thymic progenitors are infected with ICN retrovirus, transplanted to recipient mice, and monitored for circulating DP thymocytes. Once signs of T cell leukemia are present, the animals are injected with tamoxifen to activate Cre recombinase and induce deletion of the mir-181a-1/b-1 allele. The animals are monitored for circulating DP thymocytes. It is expected that the percentage of DP cells will decrease and extend the lifespan of these animals.

Example 2

MiR-181a potentiates early αβ T cell development Among many known hematopoietic miRNAs, miR-181a is preferentially expressed in the B cell but not T cell lineages in the mouse bone marrow. Ectopic expression of miR-181a in hematopoietic stem/progenitor cells results in a marked increase in B cell differentiation, while accompanied by a decrease in the percentage of T lymphocytes in the peripheral blood of transplanted mice. Interestingly, miR-181a is also strongly expressed in the mouse thymus, which consists mainly of T cells, suggesting that miR-181a may play some role in the development and function of T cells. Here we show that miR-181a, a member of an abundant class of ~22 nucleotide endogenous small regulatory RNAs, can quantitatively modulate T cell development.

T cell differentiation in the thymus can be divided into discrete stages characterized by the expression of CD4 and CD8 coreceptors. CD4 and CD8 double-negative (DN) cells, which are the early T cell progenitors in the thymus, can differentiate into CD4 and CD8 double positive cells (DP), and then further differentiate into mature CD4 or CD8 single-positive (SP) cells. DN cells can be further fractionated based on the expression of CD44 and CD25 into DN1 ($CD44_+$ $CD25_-$), DN2 ($CD44_+$ $CD25_+$), DN3 ($CD44_-$ $CD25_+$), and DN4 ($CD44_-$ $CD25_-$) cell populations, in the order of their appearance during development. Thymic T cell populations may be sorted by FACS according to surface marker expression.

To understand the role of miR-181a in T cell development, we applied a gain-of-function approach and monitored development of thymic progenitors overexpressing the miRNA when cultured with OP9-DL1 stroma cells. This in vitro co-culture system has been established to support the development of T cells from fetal liver and bone marrow precursors by providing Notch signaling that is vital for survival, expansion and differentiation of DN cells. To this end, we asked how ectopic expression of miR-181a in purified DN thymocytes would influence their development when cultured over OP9-DL1 stroma cells.

We discovered that miR-181a overexpression caused a 15-20% increase, compared to an empty vector, in the absolute percentage of DP cells among infected ($GFP^+$) thymocytes from 6 to 10 days post-initiation of co-culture (FIG. 1A, Table I). We also used miR-223 as a control for microRNA overexpression, and observed no significant differences as compared to empty vector in the distribution of DP and CD3SP thymocytes (FIG. 1A, Table I).

Figure 12:
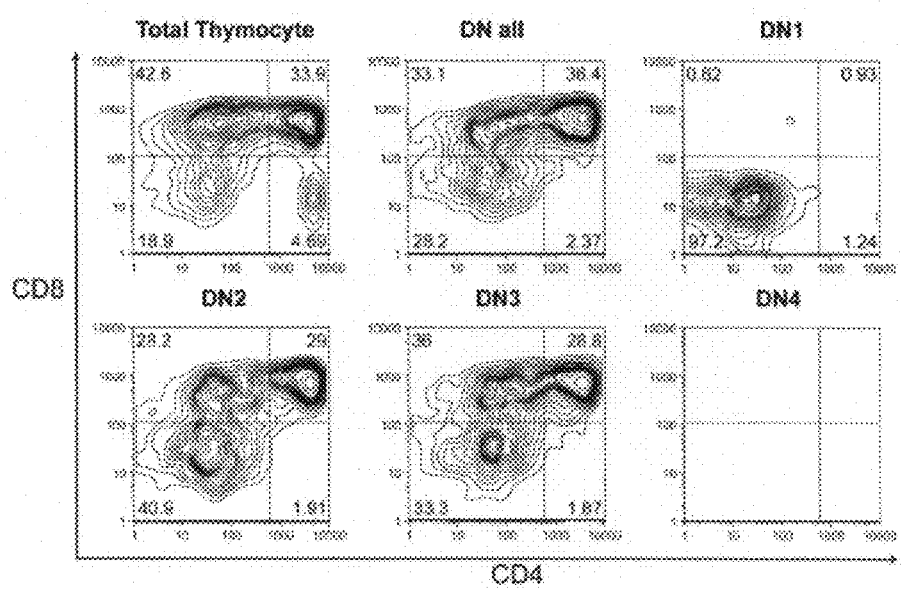
FIG. 12 DN2 and DN3 populations are necessary for thymic progenitor differentiation and expansion in the OP9-DL1 co-culture assay. FACS-sorted DN populations (DN1, DN2, DN3, DN4, and total DN) and total thymocytes were cultured over OP9-DL1 stromal cells. Representative FACS plots displaying the distribution cells expressing CD4 and CD8 following an 8 day culture.

While the thymocytes used to initiate this experiment contained all DN subpopulations, we observed that when individual DN fractions (DN1-4) were cultured over OP9-DL1 stroma cells, only DN2 and DN3 fractions displayed similar expensive and developmental properties as cultures initiated by total DN cells (FIG. 12). Therefore, DN2 and Dn3 populations might have been most affected by miR-181a overexpression.

We next asked if total thymocytes can be used to initiate this co-culture system, without pre-sorting DN thymocytes. We cultured FACS-sorted DN, DP, CD4SP, CD8SP, their respective depleted fractions, as well as unseparated total thymocytes onto OP9-DL1 stroma cells (FIG. 10A). The amount of cells plated was equivalent to their percentage in $1 \times 10^5$ total thymocytes. We observed that only fractions containing DN thymocytes (unseparated, DN, DP-depleted, CD4-depleted, and CD8-depleted thymocytes) were able to expand significantly following 8 days of culture. Furthermore, the DN-containing fractions differentiated and displayed similar absolute percentages of DN, DP, CD4SP, and CD8SP at the end of culture (FIG. 10C).

Based on the above co-culture system, we discovered that the use of total thymocytes to ectopically express miR-181a displayed similar effects as compared to experiments initiated by sorted DN cells. These miR-181a-mediated effects included a significant increase in the absolute percentage of DP thymocytes at day 8 post-culture when compared to empty vector control (FIG. 1C, 27.9% vs. 44.9% median, P=0.0014). Concomitantly, we observed a decrease in the percentage of CD8SP T cells during the same time frame, suggesting that miR-181a acts to promote the development of DP cells but prevent further maturation into CD8SP T cells (FIG. 1D). Ecotopic expression of miR-181a consistently caused a 15-20% increase in the fraction of DP cells. We normalized the data for comparison between different sets of experiment by converting absolute percent values into a relative change in the percent DP thymocytes. This is achieved by setting baseline (empty vector) to zero and miR-181a functional activity to one. Normalization allowed for the quantification of effects of each expression construct for the remainder of the study.

Figure 11:
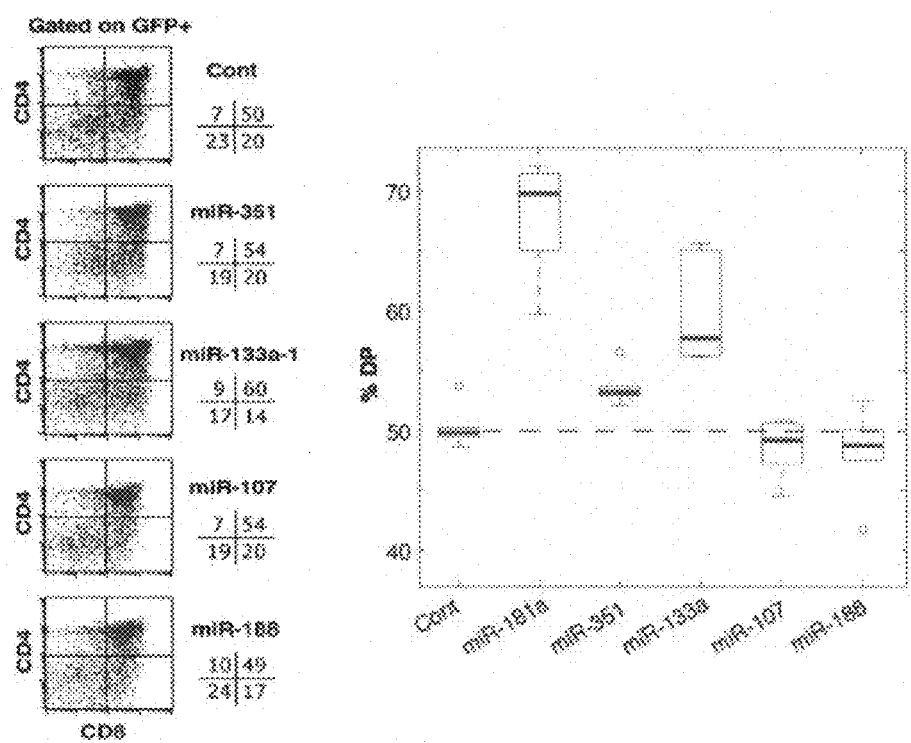
FIG. 11 Ectopic expression of other thymus miRNAs did not augment early T cell development. Thymocytes infected with miR-181a, miR-351, miR-133a-1, miR-107, and miR-188 expression constructs were analyzed for the absolute % DP thymocytes remaining in culture after 8 days. Data are displayed as box plots with the red line representing the median (n=12). P values were determined using the Mann-Whitney rank sum test as compared to vector control.

The ability to enhance DP development was specific for miR-181a, as overexpression of other miRNAs cloned from thymocytes (miR-351, miR-133a-1, miR-107, miR-188) did not elicit the same phenotype (FIG. 11). Furthermore, miR-181a's activity was abolished with mutations introduced to nucleotides 2-7 from the 5' end of the mature miRNA, also known as the 'seed' region (FIG. 1B-D). The elimination of functional activity was not due to the reduction of expression as both the wild type and mutant miR-181a are produced at similar levels according to Northern blot analysis (FIG. 1E).

Taken together, we demonstrated that overexpression of miR-181a in thymic progenitors from total thymocytes or total DN cells enhanced DP thymocyte development.

Example 3

Nrarp is a candidate target for miR-181a. Using a bioinformatic algorithm to predict potential miRNA pairing sites on target genes, we searched for putative binding sites present on known regulators of the Notch signaling pathway, and found that Nrarp, Numb, Numb-like, Hes6, and Lunatic Fringe (LFNG) each contain multiple miR-181a binding sites in the 3' UTR region (FIG. 2B, FIG. 13A-D).

To assess the role of these candidate genes in T cell development, we transduced thymic progenitors with retroviral constructs expressing only the coding region of these genes in the OP9-DL1 co-culture assay. We discovered that ectopic expression of only Nrarp-ORF was able to profoundly block the development of DP thymocytes when compared to vector control (FIG. 2A; 0.0 vs. 1.1 media normalized DP value, P<0.0001).

Figure 2:
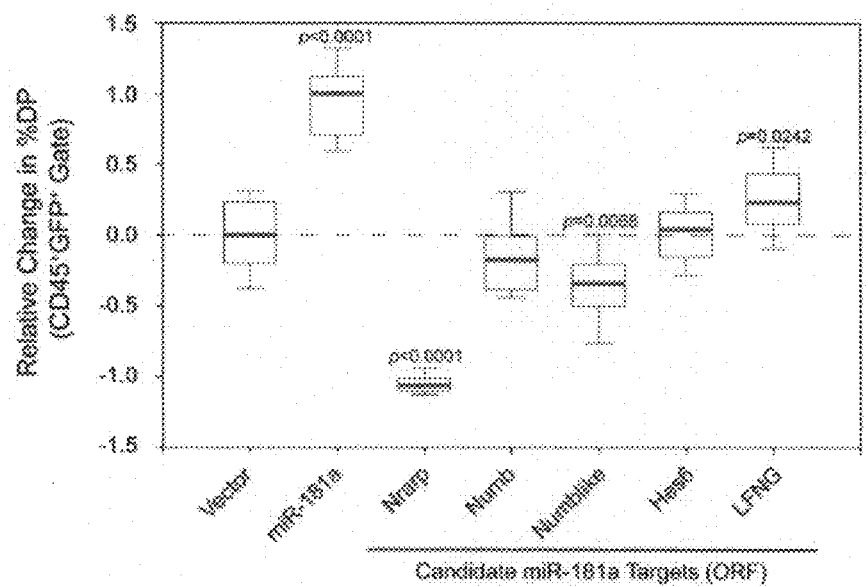
FIGS. 2A-2D miR-181a targets Nrarp, a negative regulator of the Notch signaling pathway. (A) Signaling molecules of the Notch pathway that possess putative miR-181a binding sites are candidates for regulation by miR-181a. The coding region of each candidate target gene was overexpressed in the OP9-DL1 co-culture assay and monitored for their effects on DP development. Box plots describe the relative change in the % DP thymocytes (n=12). Representative analysis of three independent experiments is shown. (B) The mouse Nrarp gene contains three purported miR-181a binding sites (T1, SEQ ID NO:3, T2, SEQ ID NO:4 and T3, SEQ ID NO:4) located in their 3'UTR based on our computational analyses. The predicted base pairing between miR-181a and Nrarp are displayed. Mutations on the Nrarp gene were designed to disrupt binding with the seed region of miR-181a and used for the overexpression study in (D). (C) Western blot analyses confirm the regulation of Nrarp protein expression by miR-181a. Cell lysates were obtained from T6E cell lines stably expressing HA-tagged Nrarp-FL and miR-181a or miR-181a$^{mut}$. Relative Nrarp protein levels were determined by densitometry and normalized to β-actin loading control. (D) To determine the significance of predicted miR-181a binding sites on Nrarp function, three forms of Nrarp (FL$^{wt}$, FL$^{mut}$, and —ORF) were overexpressed and examined for their effects on DP development. Relative changes in % DP are displayed as box plots (n=48; replicates pooled from four independent experiments). For both (A) and (D), the red line represents the median and P values were determined using the Mann-Whitney rank sum test as compared to vector control. For (D), statistical significance was also determined between bracketed groups (P value).

We proceeded to validate the predicted miR-181a binding sites by employing a T cell leukemia cell line, known as T6E. Stable expression of full-length cDNA (FL) of Nrarp was introduced into T6E cells along with miR-181a$^{wt}$ or miR-181$^{mut}$. We observed that miR-181a$^{wt}$ caused ~50% repression of Nrarp protein levels as compared to miR-181$^{mut}$ (FIG. 2C). To determine the functional significance of the predicted miR-181a binding cites in the 3' UTR region of Nrarp, we compared the effects of overexpressing full length Nrarp (ORF+3'UTR) to that of the coding region (ORF only). Nrarp-FL$^{wt}$ containing intact predicted miR-181a binding sites was found to nearly eliminated the suppressive activity of Nrarp when compared to ORF overexpression (FIG. 2D; −0.53 vs. −2.12 median normalized DP value, P<0.0001). When nucleotides predicted to pair with the seed region of miR-181a were mutated (FIG. 2B), the inhibition of DP development was recovered, displaying 150% increase repressive activity as compared to FL$^{wt}$ (FIG. 2D: −1.28 vs. −9.51 median normalized DP value, P=0.0008).

Figure 14:
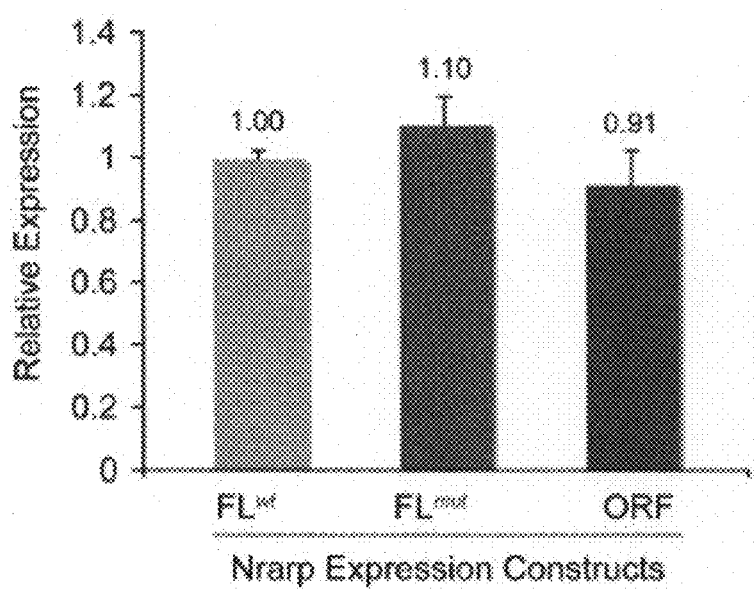
FIG. 14 Similar levels of Nrarp produced from different expression constructs. Nrarp expression constructs ($FL^{wt}$, $FL^{mut}$, ORF) were transfected into BOSC23 cells for 48 h. Total RNA was then isolated and quantitative RT-PCR was performed to determine the levels of Nrarp transcripts. Samples were normalized to GFP expression and data is presented as expression relative to Nrarp-FL-wt construct (mean±sd, n=3).

Moreover, quantitative PCR analysis showed that the expression constructs containing the FL$^{wt}$ and FL$^{mut}$ produced similar levels of Nrarp transcripts. Therefore, the differential functional activities are likely due to altered regulation of Nrarp-FL caused by endogenous miR-181a (FIG. 14). In fact, Nrarp production from the ORF construct was ~9% lower than either FL$^{wt}$ and FL$^{mut}$, yet the ORF construct was still the most efficient at inhibiting the development of DP thymocytes.

Figure 3:
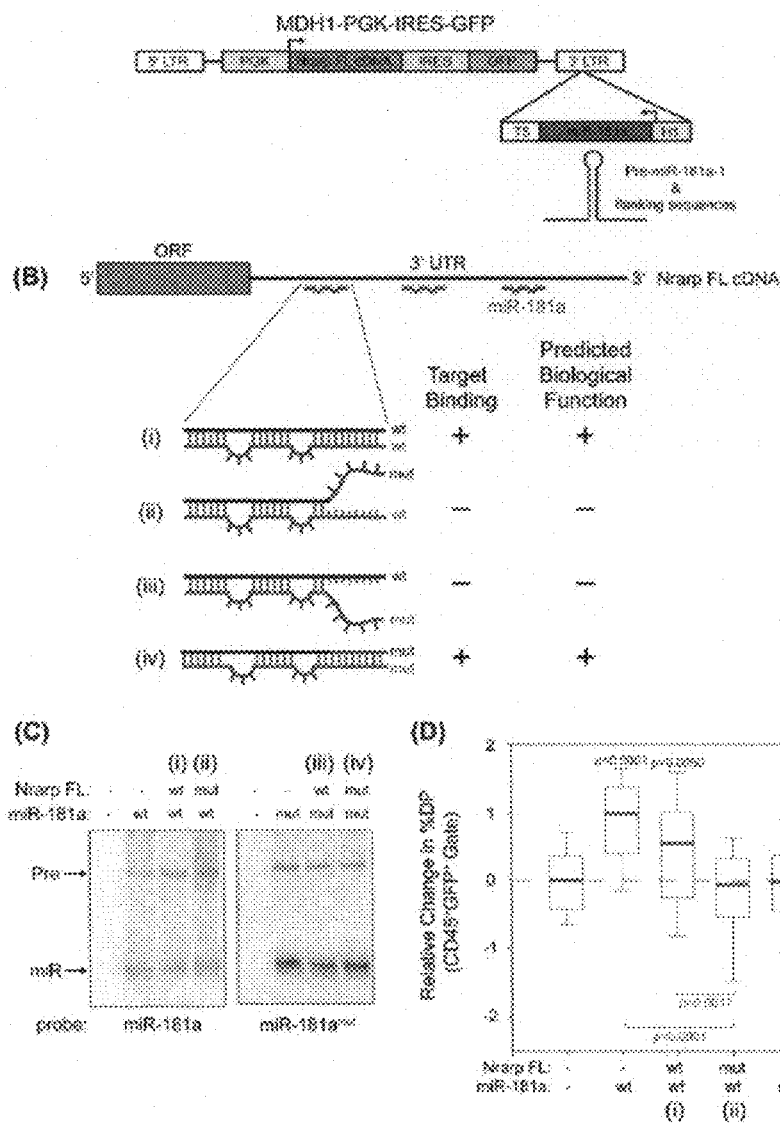
FIGS. 3A-3D Epistatic analyses reveal a direct regulation of Nrarp by miR-181a. (A) Schematic diagram of the retroviral vector (MDH1-PGK-IRES-GFP) used for the simultaneous co-expression of a miRNA and its target gene. Pre-miR-181a-1 along with ~125 nt native flanking sequences was inserted in the H1 expression cassette, whereas the Nrarp-FL cDNA is expressed as a bicistronic message along with GFP. The constitutive expression of GFP from the PGK promotor served as a surrogate marker for infection. (B) Schematic diagram describing the four possible epistatic interactions (i-iv) between Nrarp and miR-181a, as well as their predicted biological outcome. (C) Northern blot analyses demonstrate that epistatic constructs produce comparable levels of wild type and mutant miR-181a. Total RNA from BOSC23 cells transfected with epistatic constructs were isolated and probed with DNA oligos against miR-181a and miR-181a$^{mut}$. (D) Epistatic analyses indicate that the direct regulation of Nrarp by the miR-181a is mediated through the predicted miR-181a binding sites on 3' UTR of the Nrarp gene. Epistatic constructs expressing various combinations of Nrarp and miR-181a were introduced into thymic progenitors by retroviral transduction. Their effects on DP cell development were evaluated in the OP9-DL1 co-culture assay. Data from 4 independent experiments (each with 12 independent replicates, total 48 replicates) were pooled and presented in the box plots. Mann-Whitney Rank Sum Tests were performed to determine whether the activities of indicated constructs were statistically different from those of the control vector (P value) and miR-181a$^{mut}$ only (P value). Statistical significance was also determined between bracketed groups (P value).
Figure 15:
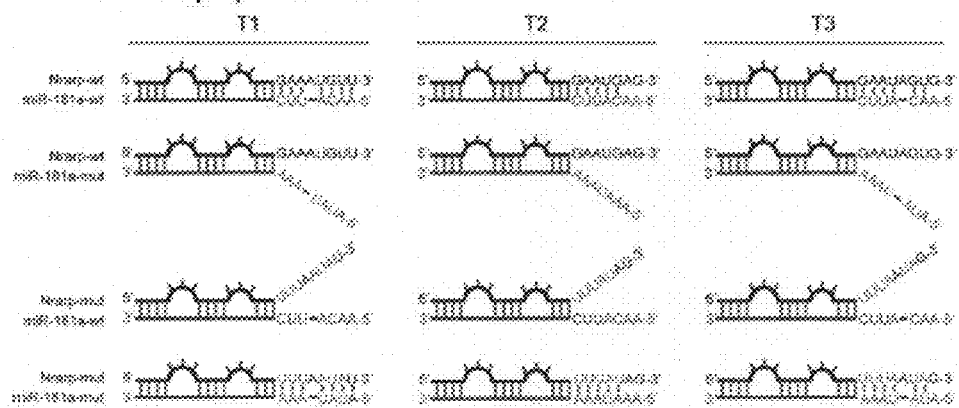
FIG. 15 Epistatic interactions between miR-181a and Nrarp. Schematic diagrams depicting the epistatic interactions between miR-181a and three predicted miR-181a binding sites (T1, T2, and T3) on 3'UTR of the Nrarp gene. RNA base pairing in the seed region are displayed. Angled nucleotides are used to emphasize disruption of seed pairing region.

Epistatic analysis demonstrated a direct regulation of Nrarp by miR-181a. To further validate Nrarp as the functional relevant target for miR-181a during T cell development, we performed epistatic analysis to manipulate the miR-181a-Nrarp interaction through mutagenesis and tested the functional implications of such modifications (FIGS. 3B and 15). Simultaneous expression of the miRNA and its candidate target gene was achieved by cloning the Nrarp-FL downstream to the PGK promoter, while the miR-181a was inserted in the H1 expression cassette of the MDH1-PGK-IRES-GFP vector (FIG. 3A). Co-expression of miR-181a$^{wt}$ with a miR-181a-insensitive form of Nrarp-FL (Nrarp-FL$^{mut}$) abolished the functional activity of miR-181a back to baseline level (empty vector) (FIG. 3D: 1.0 vs. −0.07 median normalized DP value, P<0.0001). This indicates that miR-181a is unable to regulate the Nrarp-FL$^{mut}$, thereby allowing unregulated Nrarp to prevent DP development.

However, when miR-181a$^{wt}$ is co-expressed with Nrarp-FL$^{wt}$, the miR-181a-mediated regulation of Nrarp is intact, resulting in an increase in DP development (FIG. 3D; 0.54 vs. −0.07 median normalized DP value, P=0.0017). Similarly, when the seed mutant form of miR-181a is co-expressed with the Nrarp-FL$^{wt}$, the disrupted interaction allows unregulated Nrarp to reduce the percentage of DP thymocytes as compared to miR-181a$^{mut}$ alone (FIG. 3D; −0.01 vs. −0.98 median normalized DP value, P<0.0001). More importantly, by restoring the interaction through compensatory mutations on both the miRNA and its target, we observed a 41% reversal of suppression (FIG. 3D; −0.98 vs. −0.57 median, P=0.0013).

Example 4

Specific silencing of Nrarp does not recapitulate miR-181a function. In order to find other targets of miR-181a, we used short hairpin siRNA (shRNAs), designed specifically to silence Nrarp protein expression, and tested their abilities to recapitulate the miR-181a phenotype. Among the three shRNA constructs designed against the Nrarp gene, the two directed towards the 3'UTR nearly completely eliminate Nrarp protein levels as measured by Western blot analysis (FIG. 4A). However, they were unable to recapitulate the increase of DP thymocyte development in the OP9-DL1 co-culture assay (FIG. 4B) even though these shRNAs directed toward the 3'UTR were more efficient than miR-181a at Nrarp protein expression.

MiR-181a targets phosphatase genes of the pre-TCR signaling pathway. We reasoned that miR-181a function to coordinately regulate both Notch and pre-TCR pathway during early T cell development. Repression of several phosphatases along the TCR signaling pathway is implicated in TCR signaling in mature T cells. To determine whether these phosphatases are relevant targets for miR-181a during early T cell development, we overexpressed different version of these phosphatases in the Op9-DL1 co-culture assay. In the absence of a 3'UTR, ectopic expression of only the coding region of the DUSp5, DUSP6, SHP2, and PTPN22 all were able to efficiently reduce the development of DP thymocytes (FIG. 5A). This inhibition was abolished with the overexpression of the full length cDNA versions of these phosphatases and partially restored by mutating the miR-181a binding site in the 3'UTR (FIG. 5A). Cumulatively, this data demonstrated that the suppressive activity of each phosphatase is dependent on the absence of cognate interaction between miR-181a and the phosphatase gene. Furthermore, similar to the selective knockdown of Nrarp, shRNAs against SHP2, DUSP5, and DUSP6 genes were unable to recapitulate the miR-181a phenotype (FIG. 5B). This observation emphasizes the importance of multi-target regulation by miR-181a to potentiate early T cell development.

Materials and Methods

Mice. C57BL/6 mice were obtained from Jackson Laboratory and maintained at the Stanford University Department of Comparative Medicine Animal Facility in accordance with National Institutes of Health guidelines.

Antibodies for FACS and Western Blot Analyses. For FACS analysis, the following fluorescent-conjugated antibodies were from eBiosciences (San Diego, Calif.): α-B220-FITC (RA3-6B2), α-CD3β-FITC (145-2C11), α-CD4-FITC (RM4-5), α-CD8α-FITC (53-6.7), α-CD11b-FITC (M1/70), α-TER119-FITC (TER-119), α-CD4-PECy5.5 (RM4-5), and α-CD8α-APC (53-6.7). The following antibody reagents were from BD Pharmingen (San Jose, Calif.): α-Gr-1-FITC (RB6-8C5), α-Sca1-FITC (E13-161.7), α-CD45-PE (30-F11), α-CD44-PECy5 (IM7), α-CD25-APC (PC61), α-CD5-APC (53-7.3), α-CD69-biotin (H1.2F3), α-TCRβ-biotin (H57-597), and Streptavidin-APC. For Western blot analysis, the following antibodies were used: α-HA rabbit monoclonal antibody (DW2; Upstate; Temecula, Calif.), α-Rabbit IgG (H+L)-HRP goat polyclonal antibody (Zymed Laboratories; South San Francisco, Calif.), and α-mouse β-actin rabbit polyclonal antibody (AbMart; Shanghai, China).

Plasmid Construction. We used retroviral expression vectors containing a murine stem cell virus backbone for the ectopic expression of miRNAs and/or target genes. For the sole expression of miRNA, pri-miRNA genes were cloned into the human H1 expression cassette of retroviral expression vector MDH1-PGK-GFP 2.0. Pri-miRNA containing ~22-nt mature miRNA with 125-nt of flanking genomic sequences was PCR-amplified from mouse genomic DNA and determined to be expressed via Northern Blot analysis (Min and Chen, 2006). MiR-181a$^{mut}$ was generated by altering the 2nd to 7th nucleotides from the 5' end of the mature miR-181a as indicated in FIG. 1A. Compensatory mutations were introduced to the miR-181a* strand to preserve the secondary structure of pre-miR181a. Cells expressing the miRNA can be monitored by GFP which is constitutively expressed from the murine 3-phosphoglycerate kinase promoter (PPGK). For Notch target gene overexpression, the coding region was cloned downstream to the mouse PPGK and expressed as a bicistronic message, with GFP placed after the EMCV IRES (internal ribosomal entry site) in the MDH1-PGK-IRES-GFP vector (FIG. 3A). Nrarp open reading frame (ORF) region was PCR-amplified from a Full-length Mammalian Genome Collection (MGC) Clone (IMAGE 5391567; Accession BC069891; nt 107-451). Numb and Numb-like coding regions were PCR-amplified from plasmids containing their respective full-length cDNAs. A plasmid containing the full-length cDNA for Lunatic Fringe (LFNG) was used as a template to amplify the ORF. Overexpression constructs for SHP-2, DUSP5, DUSP6, and PTPN22 were generated as described in Li et al. (Li et al., 2007). For construction of epistatic constructs, full length cDNA of Nrarp and miRNA were expressed from mouse PGK and human H1 promotors, respectively in the MDH1-PGK-IRES-GFP vector. Wild type Nrarp-FL was PCR-amplified from MGC clone (IMAGE 5391567; Accession BC069891; nt 107-2109). Nrarp-FL$^{mut}$ was generated by standard overlapping PCR to introduce mutations to the nucleotides that were predicted to bind to the seed region of miR-181a and complementary to miR-181a$^{mut}$ to restore interaction (FIG. 16).

miR-181a$^{mut}$ was generated by altering the 5' second and third nucleotides of the mature miR-181a (from (SEQ ID NO:60) 5'AACAUUCAACGCUGUCGGUGAGU3' to (SEQ ID NO:6) 5'AUAAUUCAACGCUGUCGGU GAGU3', nucleotide changes are underlined).

Compensatory mutations were introduced to the miR-181a* strand to preserve the secondary structure of pre-miR181a. Mutant miR-181a can be properly expressed and processed as indicated by Northern blot analyses.

Antibodies and fluorescent reagents. α-mouse PTPN22 polyclonal antibody was a kind gift from Dr. A. Chan and Dr. K. Hasegawa (Genentech). PE-streptavidin, PECy5-streptavidin, biotin-α-CD3ε, biotin-α-CD28, biotin-α-H-2 K$_b$, biotin-α-IL-2, α-CD16/32, α-B7.1, α-B7.2, α-IL-2, FITC-α-CD4, PE-α-CTLA4, α-Lck PY505, PE-α-phospho-ERK1/2 and their isotype controls were from BD Pharmingen. Biotin-syrian hamster IgG control and FITC-conjugated Donkey anti-Rabbit IgG were from Jackson ImmunoResearch. Streptavidin was from Prozyme. For cross-linking experiments, azide was dialyzed away before use. α-Lck (3A5, for immunoprecipitation), α-SHP-2 (polyclonal) and α-phosphoserine (polyclonal) were from Upstate/Chemicon. <-DUSP6 (polyclonal), α-actin and α-Lck (polyclonal for immunoblotting) were from Santa Cruz Biotech. α-PY416 of Src family (PY394 of Lck) and anti-ppERK (T202/Y204) rabbit monoclonal antibody (197G2) were from Cell Signaling Technology. α-DUSP5 was from ABcam. α-SHP-1 (polyclonal) was from R&D Systems. The calcium indicator Fura-2-AM was purchased from Molecular Probes.

Generation of Stable Expressing T6E Cell Lines. To validate repression of Nrarp by miR-181a via Western Blot analyses, the Nrarp protein was tagged with two copies of HA (a.a. YPYDVPDYA, SEQ ID NO:69) on the amino terminus and separated by amino acids (SEQ ID NO:70). The HA-Nrarp-FL was inserted downstream to PPGK in the MDH1-PGK-IRES-GFP and transcribed as a bicistronic message along with GFP. MiR-181a or its mutant form was simultaneously expressed from the H1 expression cassette on the same vector. These co-expression constructs were packaged into retroviral viruses and used to infect T6E cell lines. GFP positive cells were FACS-sorted to establish a stable expressing cell line that was used for Western Blot analysis.

Sorting of Thymocyte Populations. Major thymocyte populations (DN, DP, CD4SP, and CD8SP) were fractionated based on their expression of CD4 and CD8. For sorting DN1-4, total thymocytes were first enriched for total DN thymocytes by the depletion of cells expressing either CD4 and/or CD8 labeled with magnetic microbeads (Miltenyi Biotec, Auburn, Calif.). Negative selection was performed using an autoMACS™ Separator (Miltenyi Biotec). Cells depleted of CD4/CD8 were then stained for lineage markers (CD3, CD4, CD8, CD11b, B220, Ter119, and GR1) and for CD25 and CD44 surface molecules that define DN subpopulations: DN1 (Lin-CD25-CD44$^+$), DN2 (Lin-CD25+CD44$^+$), DN3 (Lin-CD25$^+$CD44$^-$), and DN4 (Lin$^-$CD25$^-$ CD44$^-$). In all experiments, propidium iodide was used to exclude dead cells and doublets. Cells were sorted at the Stanford Shared FACS Facility using the Flasher II, a hybrid instrument in which a FACS II bench is coupled to FACS DiVa electronics (BD Biosciences, San Jose, Calif.). Each sorted population were >95% pure.

shRNA Design. Three shRNA constructs were designed against different locations on the Nrarp gene (ORF1, 394-412; UTR1, 892-910; UTR2, 971-989). Invitrogen BLOCK-iT™ RNAi Designer (rnaidesigner.invitrogen.com/rnaiexpress/) was used to find the candidate targeting sequences and further selected based on the guidelines previously described (Li et al., 2007). Short hairpin RNAs against SHP2, DUSP5, and DUSP6 used in this study were generated as previously described (Li et al., 2007).

Transfection of BOSC23 cells. BOSC23 cell line was used for transient transfection to generate retrovirus and for subsequent Northern Blot and Western Blot analyses. In each case, 5×10$^5$ BOSC23 cells were plated on each well of a 6-well plate 12 h prior to transfection using FuGENE reagent (Roche Applied Science, Indianapolis, Ind.). For retroviral packaging, 2 μg of expression constructs (miRNA and/or target gene) were co-transfected with 1 μg pCLeco packaging vector. Retrovirus-containing supernatant was harvested at 48 h and immediately stored at −80° C. in 1 ml aliquots. BOSC23 cells were lysed in TRIzol Reagent (Invitrogen, Carlsbad, Calif.) for Northern Blot analyses as previously described in detail (Min and Chen, 2006). To validate the shRNA-mediated knockdown of Nrarp protein expression, 2 μg of shRNA against the Nrarp gene (FIG. 4A) were co-transfected with 1.25 μg of HA-Nrarp-FL expression construct. Cell lysate was harvested after 48 h for Nrarp protein expression using Western blot.

OP9-DL1 Co-Culture Assay. The OP9-DL1 in vitro co-culture assay was previously described in detail (Mao and Chen, 2007). Briefly, six to eight-week old male C57BL/6 mice (Jackson Laboratory, Bar Harbor, Me.) were primed with a single dose of 5-fluorouracil (5-FU; 150 mg/kg body weight; Sigma-Aldrich, St Louis, Mo.) via the retro-orbital injection. Thymocytes are harvested following 4 days of 5-FU priming and transduced with retroviral supernatant via spin infection at 2000 rpm for 2 hours at room temperature. To assist in retroviral infection, polybrene (Sigma-Aldrich) was supplemented at a final concentration of 4 μg/ml. After centrifugation, thymocytes were resuspended in Minimum Essential Medium-α(α-MEM; Invitrogen) containing 20% Characterized FBS (Hyclone, Logan, Utah), 5×10$^{-5}$ M 2-Mercaptoethanol (Invitrogen), 10 mM HEPES Buffer Solution (Invitrogen), 1 mM Sodium Pyruvate (Invitrogen), 5 ng/ml IL-7 (PeproTech, Rocky Hill, N.J.) and 27.5 ng/ml Flt3-Ligand (PeproTech). One hundred thousand thymocytes were seeded in each well of a 24-well plate containing a confluent monolayer of OP9-DL1 stromal cells. For each experiment, twelve replicate cultures were performed for each miRNA expression construct. Thymocyte culture media were replaced after one day and replenished on day 6 of the co-culture. On day 8, thymocytes and stromal cells were resuspended into a homogeneous mixture by forceful pipetting assisted by enzymatic action of collagenase type IV (0.8 mg/ml for 15 minutes at 37° C.; Worthington Biochemical Corp., Lakewood, N.J.). It was determined that such collagenase exposure did not affect antigen detection by antibodies used for flow cytometry. FACS analysis was used to determine the fraction of differentiating thymocytes expressing CD4 and/or CD8 remained in culture. Since the OP9-DL1 cell line also expresses GFP, we also stain for CD45 to differentiate thymocytes from stromal cells.

Quantitative RT-PCR for miR-181a and Target Gene Expression Analysis. FACS-sorted murine DN, DP, CD4SP, CD8SP, and DN1-4 thymocytes were immediately lysed in TRizol Reagent (Invitrogen). Total RNA was isolated according to manufacturer's instruction. For target gene expression analyses, first strand cDNA synthesis was performed using High Capacity cDNA Reverse Transcriptase Kit (Applied Biosystems, Foster City, Calif.) according to manufacturer's instruction. Single-stranded cDNA template was then amplified using TaqMan® Universal PCR master mix (Applied Biosystems) containing a final concentration of 900 nM primers and 250 nM of TaqMan® probe. Real-time PCR was performed on an ABI Prism 7700 Sequence Detection System (Applied Biosystems) and data were analyzed using Sequence Detector Software 2.1 (Applied Biosystems). For each sample, GAPDH amplification (Applied Biosystems) was used to normalize the amount of cDNA input. Amplification primers and TaqMan® probes were designed to span the exon-exon junctions to prevent amplification of genomic DNA (Table II). To measure mature miR-181a expression, purified thymocytes were spiked with a synthetic miR-223 standard at a fixed ratio of pmol/cell prior to total RNA isolation. TaqMan miRNA assays (Applied Biosystems) were then used to quantitate miRNA expression in each cell population using standard curve methods.

Statistical Analysis. For most of the OP9-DL1 co-culture analyses, the absolute % DP from individual cultures was converted to a relative change in the % DP by setting functional activities of the empty vector to zero and miR-181 to one. Relative change in the % DP or absolute % DP are displayed as box plots, with the ends of the boxes defining the 25th and 75$^{th}$ percentiles, a red line indicating the median, and bars defining the 5th and 95th percentiles. Statistical analyses were performed using InStat3 software program (GraphPad Software, San Diego, Calif.). P values for box plots were determined using the Mann-Whitney rank sum test. All other statistical analyses were performed using unpaired student's t-test.

Example 5

Pre-miRNA Loop Nucleotides Control the Distinct Activities of mir-181a-1 and mir-181c Mature miRNAs can often be classified into large families consisting of members with identical seeds (nucleotides 2 through 8 of the mature miRNAs) and highly homologous ~21-nt mature miRNA sequences. However, it is unclear whether members of a miRNA gene family, which encode identical or nearly identical mature miRNAs, are functionally interchangeable in vivo.

It is shown herein that mir-181a-1 and mir-181c have distinct activities, which are largely determined by their unique pre-miRNA loop nucleotides, not by the one-nucleotide difference in their mature miRNA sequences. Moreover, the activity of mir-181a-1 on T cells can be quantitatively influenced by nucleotide changes in its pre-miRNA loop region. We find that both the strength and the functional specificity of miRNA genes can be controlled by the pre-miRNA loop nucleotides.

These results demonstrate that pre-miRNA loop nucleotides have a critical role in controlling the activity and the functional specificity of miRNA genes, and that members of the same miRNA gene families could have evolved to achieve different activities via alterations in their pre-miRNA loop sequences, while maintaining identical or nearly identical mature miRNA sequences.

Results

Assay for measuring mir-181a-1 activity in DP cell development. T cell development was used a functional readout to determine the nucleotides and structural domains that are required for the function of mir-181 genes. We have shown that mir-181a-1 plays important roles in T and B lymphocyte development, and can function as a "rheostat" to modulate the strength and threshold of T cell receptor (TCR) signaling. Moreover, mature miR-181a is developmentally regulated during early T cell differentiation, in the transition from CD4 and CD8 double-negative (DN) to CD4 and CD8 double-positive (DP) cells, in the thymus. Using the OP9-DL1 co-culture assay, which can recapitulate the differentiation of DN progenitors into DP cells in vitro, we showed that ectopic expression of mir-181a-1 in DN thymic progenitor cells lead to a significant increase in the percentage of DP cells, from a median level of ~57% in the control group to a median level of ~77% in the mir-181a-1 expressing group. We have found that mir-181a-1 potentiates DN to DP cell development by targeting negative regulators in the Notch and pre-TCR signaling pathways and potentiate early T cell development. This assay allowed us to quantitatively measure the contribution of nucleotide sequences and RNA structural domains to miRNA gene function.

Nucleotides in the pre-miRNA stem region have varied contribution to mir-181a-1 activity. To investigate which nucleotides of the mature miR-181a region are important for its function, we systematically mutated every set of 2-nt along its 23-nt mature miRNA region (FIG. 16A, yellow). The 2-nt sequences were altered to disrupt potential base pairings to cognate target sequences. To retain the structure of the miRNA stem-loop precursor, we simultaneously mutated the corresponding 2-nt on miR* strand, the complementary strand of the mature miRNA. Thus, these "stem mutants" contain mutations on both the mature miRNA strands and the miR* strand, affecting the sequences of both pre- and mature miRNA species. Northern analyses of transfected BOSC23 cells demonstrate that the mature miR-181a can be produced from all the mutant constructs (FIG. 16B). The varied intensities of the mature miR-181a and its mutants may not indicate the differences in actual expression levels since different oligo nucleotide probes used to detect each of the miR-181a mutant forms. When a shorter probe that matches perfectly to both wild-type mir-181a-1 and M1 was used for Northern analyses, the wild-type mir-181a-1 and M1 mutant mature forms were expressed at comparable levels.

We then ectopically expressed each of the mir-181a-1 "stem mutants" in DN thymocytes and examined their effects on DP T cell development using the OP9-DL1 co-culture assay. By comparing the negative control (empty vector) to the positive control (wild-type mir-181a-1 expressing vector), it is clear that nucleotides in the stem region have different contributions to mir-181a-1 activity in promoting T cell development (FIG. 16C). The M1 and M3 seed mutants completely abolish mir-181a-1 activity, while the M2 mutant still display residual activity for promoting T cell development, demonstrating that nucleotides in the seed region play a critical role in the mir-181a-1 gene function. In comparison, 2-nt mutations outside the seed region have modest effects on mir-181a-1 activity: the M4, M5, M7, M10 and M11 mutants show a slight reduction in activity, M6 and M9 mutants have no change in activity, and the M8 mutant show an increase in activity. Thus, nucleotides outside the seed region also contribute to mir-181a-1 function but are more tolerant of nucleotide variations.

Since nucleotides outside the 5' seed region have weaker effects on mir-181a-1 activity, we then created four additional stem mutants—the segment mutants (SM1-4) with longer stretches of mutations in the mir-181a-1 stem region (FIG. 16A). As shown by Northern blot analyses, these mutants are properly expressed and processed (FIG. 16B). As expected, altering the entire seed region (SM1) completely abolishes mir-181a-1 activity in promoting DP cell development. Interestingly, segment mutants with 3' 8-nt mutated (SM3 and SM4) also have dramatic reduction in activity, while the mutant with the center 8-nt mutation (SM2) has comparable activity to the wild-type mir-181a-1 (FIG. 16C).

Figure 17:
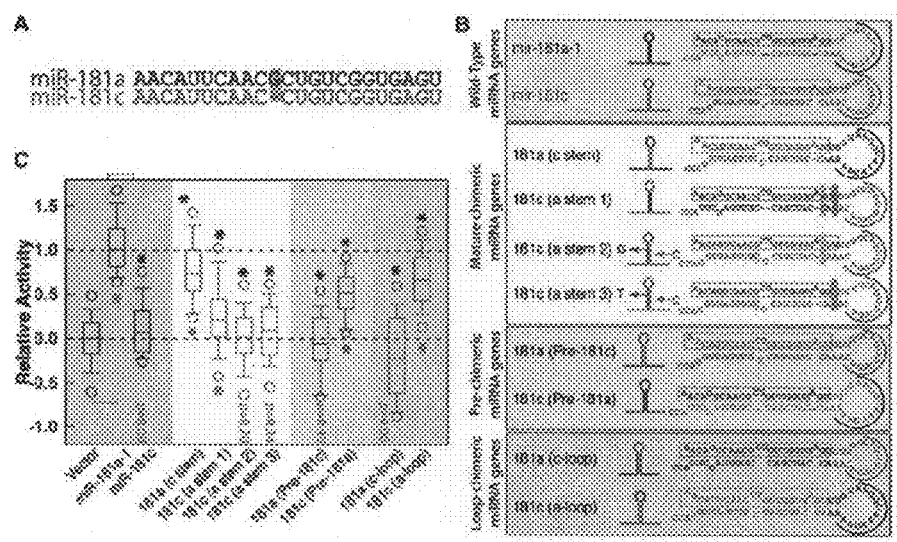
FIG. 17 The pre-miR-181a-1 loop nucleotides control the distinct activities of mir-181a-1 and mir-181c on DP cell development. (A) Nucleotide sequences of mature miR-181a and miR-181c (SEQ ID NO:1, SEQ ID NO:20). (B) Schematics and nucleotide sequences depicting the wild-type mir-181a-1 and mir-181c genes (SEQ ID NO:21-30) and corresponding precursors (shaded grey). Also shown are the chimeric miRNA genes, with the mature miRNAs, pre-miRNAs, and pre-miRNA loops swapped between mir-181a-1 and mir-181c and termed "mature-chimeric", "pre-chimeric", and "loop-chimeric", respectively. These mutant genes are designated as mir-181a (c stem), mir-181c (a stem), mir-181a (pre-181c), mir-181c (pre-181a), mir-181a (c-loop), and mir-181c (a-loop). (C) The effects of the chimeric mir-181a-1/c genes on DP cell development. Normalized data from 3-7 independent T cell assays (each with 12 independent replicates for a total of 36-84 replicates) are pooled and graphed in the distribution box plots. Mann-Whitney Rank Sum Tests were performed to determine whether the activities of the chimeric miRNA genes are statistically different from those of the negative control vector (*, p<0.0001) and/or mir-181a-1 positive control (*, p<0.0001).

Collectively, these findings demonstrate that the nucleotides in seed region are critical for mir-181a-1 activity—small alterations in the seed region cause dramatic decreases in activity. In comparison, the nucleotides in the 3' end of the mature miRNA region have smaller contributions and the nucleotides in the center of the mature miR-181a have little or no contribution to mir-181a-1 activity (FIG. 16). These findings confirmed the importance of the seed nucleotides, as shown previously by computational and biochemical analyses, thus validating the use of this assay to measure the activity of mir-181a-1 genes and to dissect the structural and functional relationships of mir-181 genes by mutagenesis.

mir-181a-1, but not mir-181c, can promote DP cell development The members of the mir-181 family of genes produce four mature miRNAs: miR-181a, miR-181b, miR-181c, and miR-181d, from three putative polycistronic genes, mir-181a-1/b-1, mir-181a-2/b-2, and mir-181c/d, respectively. The mature miRNAs of the miR-181 family, all with identical 5' seed nucleotides, differ from one another by no more than 3-nt in either the center or the 3' end of the mature miRNAs. Specifically, mature miR-181a differs from miR-181c by only one nucleotide in the center of the mature miRNA (FIGS. 17A, 17B). Thus, according to the "seed" hypothesis and the results of "stem mutant" analyses (FIG. 16), it appears that mir-181a-1 and mir-181c should have similar activities in the co-culture assay.

To test this, we examined the ability of mir-181a-1 and mir-181c in promoting DP cell development. Mature miR-181a and miR-181c have similar expression patterns during thymocyte development, though the endogenous levels of miR-181c is about 4 to 5-fold lower than that of miR-181a in the corresponding thymocytes, indicating that they are processed in thymocytes and may play roles in normal T cell development. Thus, the thymocyte system allows us to interrogate the functions of mir-181a-1 and mir-181c in a physiologically relevant mRNA and miRNA milieu. Interestingly, while the ectopic expression of mir-181a-1 results in a substantial increase in the generation of DP cells, the expression of mir-181c does not (FIG. 17C, grey), demonstrating that mir-181a-1 but not mir-181c can promote DP cell development (p<0.0001). It will be shown below that viral constructs expressing mir-181a-1 and mir-181c can produce similar levels of miRNAs.

miRNA genes encoding identical mature miRNAs can have distinct biological activities. To examine whether the single nucleotide difference in the mature miRNA regions contributes to their distinct activities of mir-181a-1 and mir-181c, we generated "mature chimeric" miRNA genes by swapping the stem regions (miR and miR* duplexes) (FIG. 17B, yellow). The resulting "mature chimeric" miRNA genes, termed mir-181a (c stem) and mir-181c (a stem 1), should express mature miR-181c and mature miR-181a, respectively. We also generated two additional "mature chimeric" genes, mir-181c (a stem 2) and mir-181c (a stem 3), by replacing mature miR-181c with mature miR-181a while maintaining the miR-181c complementary strand. Even though mir-181a (c-stem) is designed to produce mature miR-181c, we observed that this "mature chimeric" miRNA gene was still functionally active in promoting DP cell development, albeit with a median activity of ~73% of the wild-type mir-181a-1 (FIG. 17C). In contrast, the mir-181c (a stem 1) gene, which encodes mature miR-181a, had a median activity of only ~21% of the wild-type mir-181a-1, and the mir-181c (a stem 2, 3) genes had no significant activity (FIG. 17C). These results demonstrate that the distinct activities of mir-181a-1 and mir-181c are not caused by the single nucleotide difference between their mature miRNA forms. Notably, these results demonstrate that miRNA genes encoding identical mature miRNAs, such as mir-181c and mir-181a (c-stem) that encode miR-181c, or mir-181c and mir-181a (c-stem) that encode miR-181a, can have distinct biological activities.

Pre-miRNAs and their loops determine the activities of the mir-181 genes. Since mir-181a-1 and mir-181c have divergent pre-miRNA flanking and loop sequences, we then tested whether their differences in activity are determined by their unique pre-miRNAs or by flanking sequences (FIG. 17B). We generated "pre-miRNA chimeric" genes by swapping the pre-miRNA regions between mir-181a-1 and mir-181c (FIG. 17B). When tested in the OP9-DPL1 co-culture assay, the miRNA gene with pre-miR-181a, mir-181c (pre-181a), did promote DP cell development, albeit with a median activity of ~52% that of the wild-type mir-181a-1, whereas the miRNA gene with pre-miR-181c, mir-181a (pre-181c), had no activity (FIG. 17C). These results demonstrate that sequences specific to the pre-miRNAs play a key role in determining the distinct biological activities of the mir-181a-1 and mir-181c genes. However, pre-miRNA flanking sequences may also contribute to the functions of the mir-181a-1 and mir-181c genes, since the activity of mir-181c (pre-181a) is reduced relative to that of the wild-type mir-181a-1.

Since pre-miR-181a-1 and pre-miR-181c differ mainly in their pre-miRNA loop nucleotides, we next swapped the pre-miRNA loops and examined the activity of loop chimeras in the OP9-DPL1 co-culture assay (FIG. 3B, blue). We found that mir-181c (a-loop) can promote DP cell development with a median activity of ~67% that of the wild-type mir-181a-1, while mir-181a (c-loop) is inactive in promoting DP cell development (FIG. 3C, blue, Table S2), demonstrating that the distinct biological activities of the mir-181a-1 and mir-181c genes are largely determined by the differences in their pre-miRNA loops.

Figure 18:
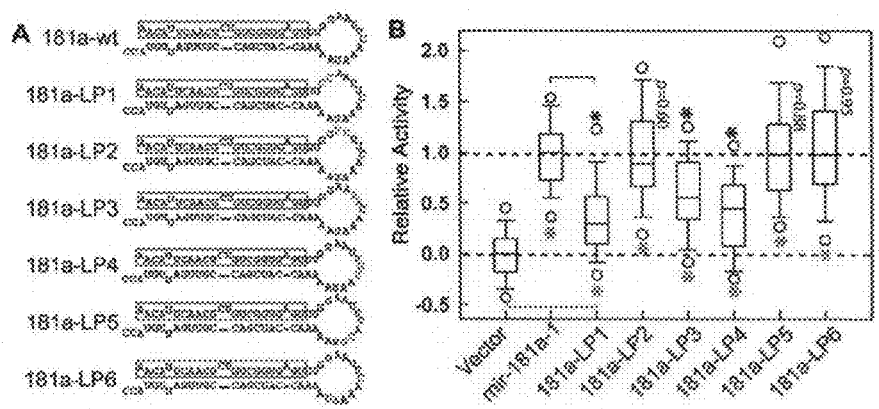
FIG. 18 The activity of mir-181a-1 is highly sensitive to nucleotide changes in its pre-miRNA loop. (A) Schematics of the pre-miR-181a-1 loop mutants (SEQ ID NO:21, SEQ ID NO:31-36). (B) The effects of pre-miR-181a-1 loop mutants on DP cell development. Normalized data from at least six independent T cell assays (each with 12 independent replicates for a total of 72 replicates) is shown. Mann-Whitney Rank Sum Tests were performed to determine whether the activities of the loop mutants were statistically different from those of the negative control vector (*, p<0.0001) and/or the mir-181a-1 positive control vector (*, p<0.0001).
Figure 19:
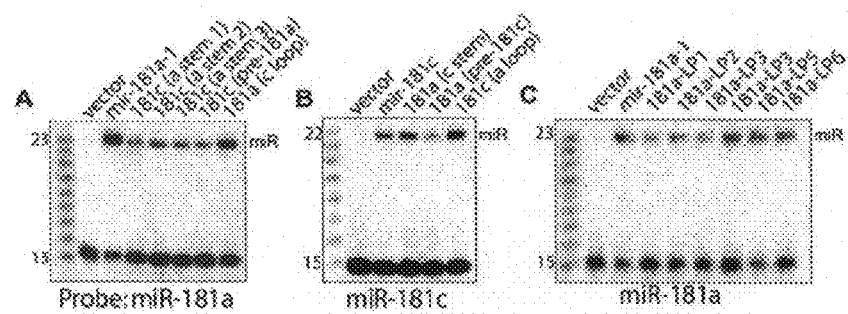
FIG. 19 Mature miRNAs produced from the mir-181a-1/c mutants have the same 5' ends. The 5' ends of mature miR-181a (A) and miR-181c (B) produced from mir-181a-1/c domain swamping mutant genes, and the 5' ends of mature miR-181a (C) produced from mir-181a-1 loop mutant genes were determined by primer extension analyses (see Materials and Methods). Synthetic miR-181a or miR-181c oligo nucleotides in single nucleotide increments (15 nt-22/23 nt) were radio-labeled and used as size ladders. The upper band represents the major cDNA product of miR-181a (23-nt) or miR-181c (22-nt), and the lower band represents radio-labeled probes for the mature miRNAs.

The mir-181a-1 activity is sensitive to nucleotide changes in its pre-miRNA loop. To further investigate the role of pre-miRNA loop nucleotides, we carried out scanning mutagenesis around the pre-miR-181a-1 loop (FIG. 18A) and found that dinucleotide mutations in the pre-miR-181a-1 loop had varied effects on mir-181a-1 activity (FIG. 18B). The 181a-LP1, 181a-LP3, and 181a-LP4 mutants had median activities of ~29%, 55%, and 46% that of the wild-type mir-181a-1, respectively (FIG. 18B). In contrast, the 181a-LP2, 181a-LP5 and 181a-LP6 mutations did not significantly affect mir-181a-1 activity. The loop mutagenesis analyses further demonstrated that pre-miRNA loop nucleotides could also quantitatively influence the activity of the mir-181a-1 gene.

mir-181a-1/c mutants produce identical mature miRNAs as their wild-type genes. To understand the mechanisms by which pre-miRNA loop nucleotides may control the activities of miRNA genes, we systematically characterized the effects of pre-miRNA loop mutations on mature miRNA biogenesis. According to computational and biochemical analyses, seed nucleotides, 5' 2-7 nucleotides of a mature miRNA are essential for target gene recognition and repression. Since the seed nucleotides are localized at the 5' end of mature miRNAs and mature miRNA often have polymorphic 3' or 5 ends as shown by miRNA cloning analyses, a few nucleotide shift in mature miRNA sequences during processing could change the seed nucleotides. To rule out that possibility that mutations in mir-181a-1/c cause shifts in the 5' end of mature miRNAs and changes the seed nucleotides, we carried out primer extension analyses and showed that mature miRNAs produced from various mir-181a-1/c mutants have the same 5' end as those produced from the corresponding wild-type mir-181a-1/c genes (FIG. 19A-C). These results demonstrate that 181a-1/c mutants do not cause changes in 5' and 3' end of the mature miRNA sequences, eliminating the possibility that mir-181a-1/c mutants affect the activities of the mir-181a-1 or mir-181c genes by controlling the fidelity of the 5' ends of the mature miRNAs produced.

Figure 6:
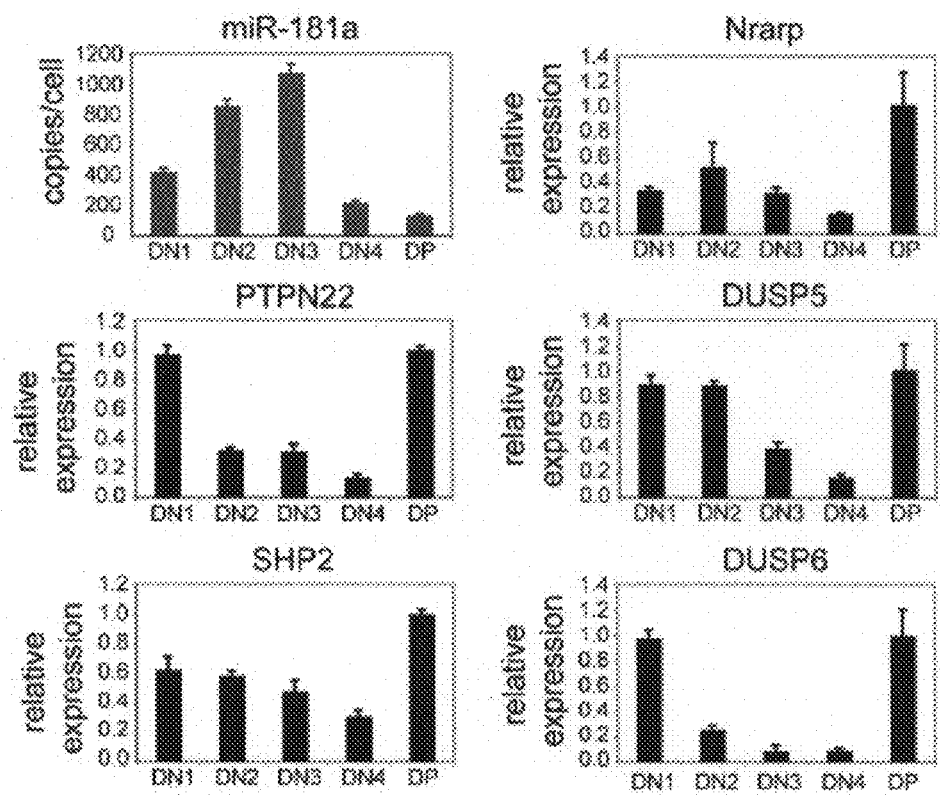
FIG. 6 Correlation of endogenous miR-181a expression with its target genes in the early thymic progenitor cell populations. Quantitative PCR was used to measure the levels of endogenous miR-181a and its relevant target mRNAs in purified thymic progenitor cell populations. Data was presented as fold difference relative to DP population (mean±SD, n=3). Representative analysis of three independent experiments is shown.
Figure 7:
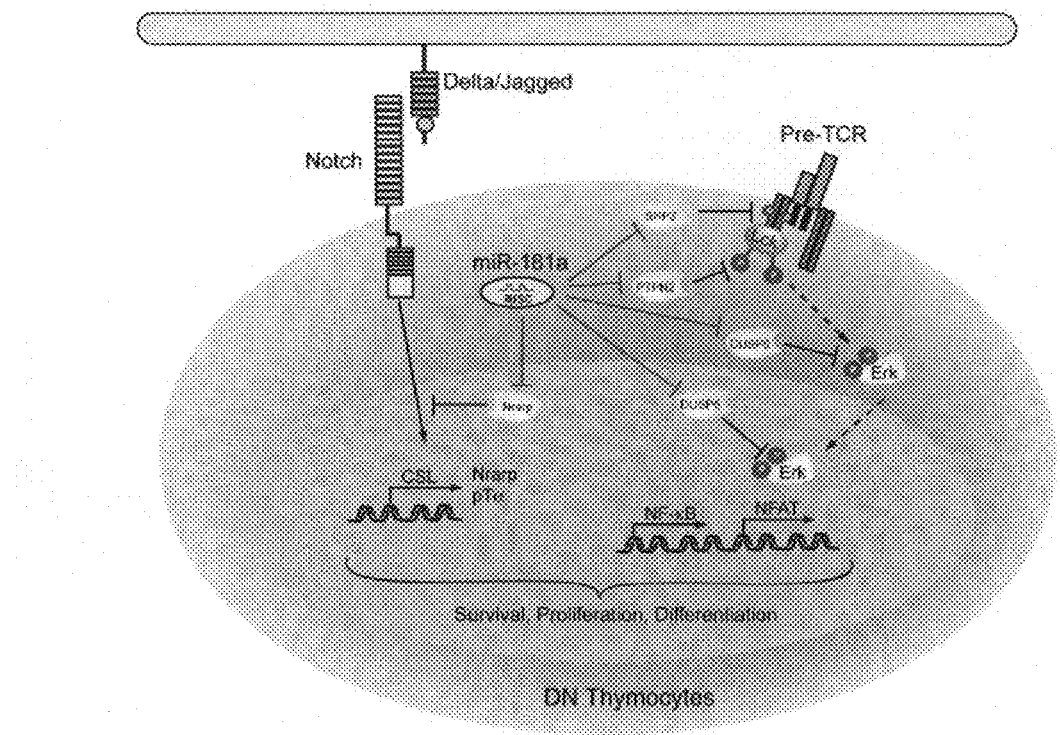
FIG. 7. Schematic diagram describing the putative mechanism of miR-181a function in early T cell development. The abundant nature of miR-181a in DN cells coordinately dampen levels of negative regulators involved in Notch and pre-TCR signaling pathways thereby maintaining active signaling through these canonical pathways to promote DP cell development.
Figure 8:
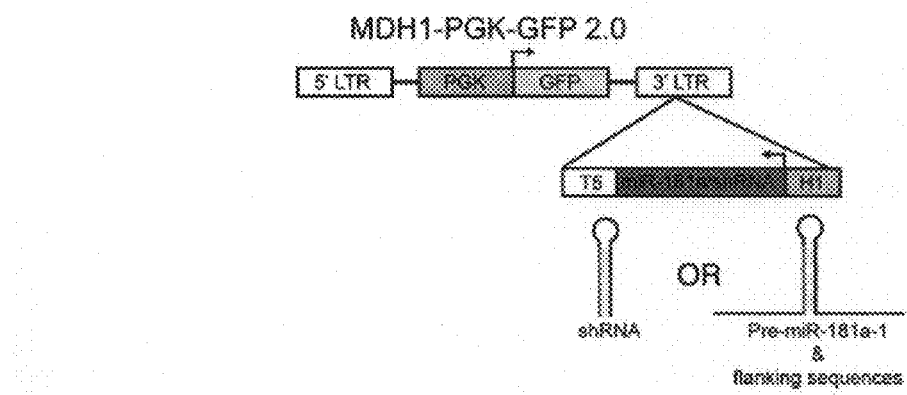
FIG. 8 Schematic diagram of the retroviral vector used for miRNAs and shRNAs expression. (A) mRNAs or siRNAs expression from pre-miRNAs or shRNAs, respectively, are driven by H1 promotor of the MDH1-PGK-GFP2.0 vector (Chen et al., 2004). miRNA genes encompass pre-miRNA and ~125 nt native flanking sequences were inserted in the H1 expression cassette. The constitutive expression of GFP from the PGK promotor served as a surrogate marker for infection.
Figure 20:
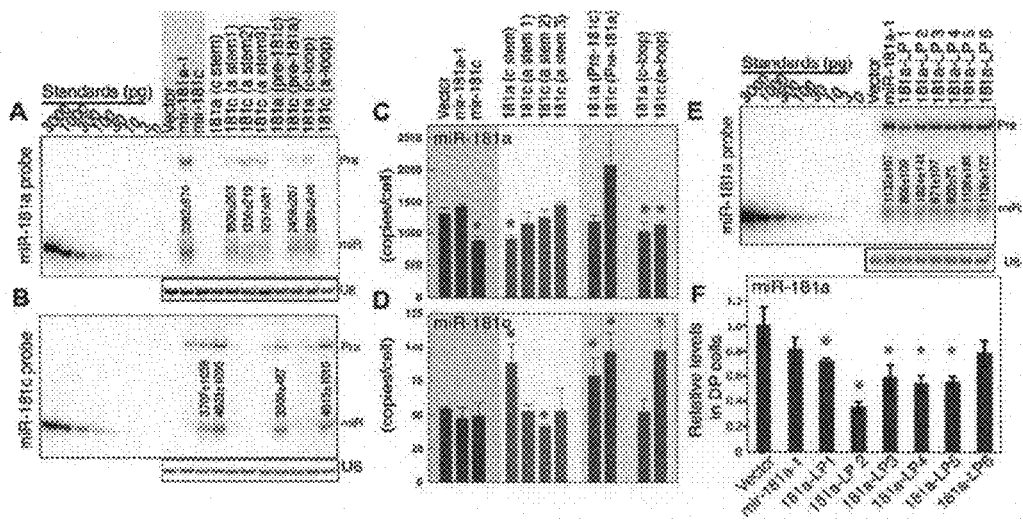
FIG. 20 The effects of mir-181a-1/c mutants on mature miRNA expression in BOSC23 and DP cells. (A, B) The copy numbers of mature miR-181a (A) and miR-181c (B) expressed in BOSC23 cells transfected with the same amounts of various viral vectors expressing different mir-181a-1/c mutants, determined by quantitative Northern blot analyses. (C, D) The copy numbers of mature miR-181a (C) and miR-181c (D) expressed in DP thymocytes transduced with viral vectors expressing various mir-181a-1/c mutants, determined by miRNA qPCR analyses. (E) The copy numbers of mature miR-181a expressed in BOSC23 cells transfected with the same amounts of various viral vectors expressing unique mir-181a-1 loop mutants, determined by quantitative Northern blot analyses. (F). The copy numbers of mature miR-181a expressed in DP thymocytes transduced with viral vectors expressing various mir-181a-1 loop mutants, determined by miRNA qPCR analyses. Statistical significance was determined by an unpaired two-tailed student's t test (compared to the control vector, *, p<0.05). Representative blots of four or more independent quantitative Northern blot analyses are shown (A, B, E).

The effects of mir-181a-1/c mutants on the levels of mature miRNA. We then investigate whether mir-181a-1/c mutants cause changes in the levels of mature miRNAs made in BOSC 23 and DP cells (FIG. 20), and if so whether these changes correlate with the activities of corresponding miRNA genes. BOSC 23 cells do not express endogenous mature miR-181a or miR-181c, thus allowing for accurate measurement of the levels of mature miRNAs produced from the mutant constructs. Quantitative Northern blot analyses were used to define the levels of mature miR-181a and miR-181c, as well as the sizes of the mature miRNAs and the levels of the pre-miRNAs, produced from various mir-181a-1/c mutant constructs in BOSC 23 cells (FIG. 6A, 6B, 6E, and S8). Since it is difficult to obtain sufficient numbers of infected DP thymocytes for Northern blot analyses, we carried out miRNA qPCR analyses to determine the number of copies of mature miR-181a and miR-181c in DP cells transduced with mir-181a-1/c mutant viruses (FIG. 6C, 6D, 6F). Comparing the effects of mir-181a-1/c mutants on the levels of mature miRNA in two different cell types also reveals whether mir-181a-1/c loop mutants cause differential miRNA processing in different cell types.

We have determined the nucleotide sequences and structural domains that are required for the function of mir-181a-1 and mir-181c through mutagenesis and domain-swapping analyses. We show that not only the nucleotides in the 5' and 3' ends of the stem but also those in the pre-miRNA loop are critical for mir-181a-1 activity. We find that mir-181a-1 and mir-181c have distinct activities in early T cell development, and the distinct activities of mir-181a-1 and mir-181c are controlled by their pre-miRNA loops, indicating that miRNA genes encoding identical or nearly identical mature miRNAs can exert different biological activities determined by their unique loop nucleotides. Interestingly, the pre-miRNA loop sequences of mir-181a-1 and mir-181c are divergent but each is evolutionarily conserved in multiple animal species, suggesting that members of the same miRNA gene families may have evolved to achieve distinct specificities or degrees of activity via alterations in their pre-miRNA loop sequences. However, mir-181a-1/c mutants do not change the 5' ends of mature miRNAs produced and the levels of mature miRNAs produced from these genes have no consistent correlation with the activities of corresponding miRNA genes. These results demonstrate that pre-miRNA loop nucleotides have a key role in controlling miRNA gene function.

Materials and Methods

Retroviral constructs for miRNA gene expression. A double-copy retroviral vector with a human H1 polymerase III expression cassette was used to express mir-181a-1, mir-181c, and their mutant genes. Briefly, a 270-nt gene segment containing a ~22-nt mature miRNA and ~125 nt of genomic sequences flanking both sides of the miRNA was amplified from genomic DNA and placed in the U3 region of the 3' LTR under the control of the human H1 pol III promoter. A GFP reporter driven by an independent murine 3-phosphoglycerate kinase promoter (PPGK) was used as a marker for infection. mir-181a-1 and mir-181c mutant constructs were generated using an overlapping PCR strategy to introduce mutations in the stem and loop regions of the miRNA genes. All mutant constructs were validated by DNA sequencing (See supporting information for the wild-type and mutant gene sequences). For mutations in the miRNA stem regions, compensatory mutations were also introduced to the miR* strands to preserve the integrity of the stem and loop structures (Fig S1). High titer retroviral supernatant was generated by co-transfecting the miRNA expression vector and pCLeco packaging construct into BOSC23 cells (293T based viral packaging cell line).

OP9-DL1 stromal co-culture assay for in vitro T cell differentiation. Six-week old male C57BL/6J mice were obtained from the Jackson Laboratory (Bar Harbor, Me.). Mice were administered a single intravenous dose of 5-fluorouracil (5-FU; 150 mg/kg body weight; SIGMA, St. Louis, Mo.) 4 days before culture initiation. Animals were treated in accordance with Stanford University and Administrative Panels on Laboratory Animal Care guidelines. Thymocytes were isolated from the 5-FU (Fluorouracil) primed-mice, infected with miRNA expression vectors by spinoculation, and seeded at $1 \times 10^5$ infected cells/well into 24-well tissue culture plates containing a monolayer of OP9-DL1 stromal cells. For each viral construct, 12 independent culture replicates were seeded. The cells were cultured in Minimum Essential Medium (MEM) Alpha Medium supplemented with 20% FCS, 10 mM Hepes, 1 mM Sodium pyruvate, 5 ng/ml IL-7, and 27.5 ng/ml Flk2/Flt3L for 24 hours and then medium was changed to remove non-adherent thymocytes. The cultures were fed with fresh medium on day 6. After about 8-10 days of culturing, cells were harvested and stained for surface marker CD4, CD8, and CD45. Percentage of DP cells yielded from culture was quantified by flow cytometry. Both adherent and non-adherent cells were collected. Adherent cells were removed by treatment with collagenase type VI (0.8 mg/ml; Worthington, Lakewood, N.J.) followed by forceful pipetting. Cells were then immunolabeled with PE-conjugated anti-CD4 antibody (clone RM4-5; BD Pharmingen, San Diego, Calif.) and PE-Cy5-conjugated anti-CD8a antibody (clone 53-6.7; BD Pharmingen) and analyzed on a FACSCalibur (BD Biosciences, San Jose, Calif.) for the expression of CD4 and CD8 cell surface antigens. GFP positive thymocytes were distinguishable from GFP positive stromal cells by FSC/SSC gate and the intensity of green fluorescence. When the infect-rate was low, anti-CD45 antibody staining was used to gate out contaminating GFP+ OP9-DL1 cells. The appropriate dilution for each antibody was determined prior to use.

Box-plots summarize the distribution of relative miRNA activity in DP cell development The ends of the boxes define the $25^{th}$ and $75^{th}$ percentiles, a line indicates the median, and bars define the $5^{th}$ and $95^{th}$ percentiles. Individual outliers are also shown. The activities of mir-181a-1, mir-181c, and mutant genes in DP cell development were normalized so that the empty vector (negative control) has a median activity of "0" and mir-181a-1 expressing vector (positive control) had a median activity of "1." The percentage of DP cells yielded from the co-culture assay varies between experiments possibly due to heterogeneous nature of the thymic progenitor cells and intrinsic variation between the batches of mice used. Therefore, such normalization is necessary to reset the baseline and allows for comparison among the independent repeats. Mann-Whitney Rank Sum Tests were performed to determine whether the activities of individual 2-nt mutants were statistically different from the control vector or the mir-181a-1 vector.

Cell culture and transfection. Adherent BOSC cells were grown in DMEM, 10% FBS, 1% of pen/strep antibiotics, supplemented with glutamine. For northern and primer extension assay, BSOC 23 cells were plated at a density of $3.75 \times 10^5$ cells/well in a 6-well plate at 24 hours before transfection. Cells were transfected with 1.25 ug constructs expressing mir-181a-1, mir-181c, c-let-7, mutant genes, and control vector using Fugene transfection reagents (Roche). The amounts of DNA transfected were equivalent to the DNA concentrations used in the luciferase reporter assays.

Quantitative Northern blot analyses. Quantitative Northern blot analyses were used to determine the level of mature miRNA expression and processing of the pre-miRNA and mature miRNA. Total RNA was prepared from BOSC 23 cells transfected with constructs expressing mir-181a-1, or mir-181c, and their mutant genes and loaded onto 15% PAGE gel (10 μg/sample). Since all of the miRNA expressing vectors contain an independent GFP reporter, percentage cells that are GFP positive were determined by FACS analyses and used to control for variations in transfection efficiency. Various amounts of synthetic mature miRNA were loaded onto the same gel to generate standard curves. Specific probes that perfectly match to mature miRNAs were used in hybridization to determine the expression of both mature and pre-miRNA species (See supporting information for probes sequences). Band intensity was determined by phosphoimager quantification. Blots were also probed with U6 probes for normalizing loading. Exact copies/pg of total RNA were determined by comparing to the corresponding standard curve. Representative blots of four or more independent quantitative Northern blot analyses were shown. Standard Curves and average results of three or more independent quantitative Northern blot analyses were summarized and plotted.

Primer Extension Analyses. Primer extension was used to map the 5' ends of the mature miRNAs produced from the mir-181a-1/c mutant genes. Total RNA was prepared from BOSC23 cells 48 hours after transfection with constructs expressing mir-181a-1, mir-181c, and their mutant genes. $^{32}$P labeled primer was mixed with appropriate RNA samples (10 ug total RNA) in the reaction buffer (1×RT reaction buffer with 0.25 mM of each dNTP), heated at 55° C. for 20 minutes, and slowly cooled to 16° C. to allow for annealing. The primer extension reaction was initiated by adding reverse transcriptase at 16° C. for 20 minutes, 42° C. for 2 hours, 85° C. for 5 minutes. Samples were loaded onto a 15% denaturing PAGE gel. Synthetic miR-181a or miR-181c oligos in single nucleotide increments (15 nt-22/23 nt) were labeled and loaded onto the gel as size ladder. The primer extension results were visualized by overnight exposure to phosphoimager screen.

miRNA qPCR analyses. In the OP9-DL1 culture assay, mixed DN (CD4⁻ CD8⁻) thymic progenitor cells differentiate into DP cells though multiple stages that are characterized by unique cell surface markers and complex molecular events. The DP cell population in the OP9-DL1 culture represents a relative homogeneous population and can be isolated by FACS-sorting in reasonable quantity for miRNA qPCR analyses. In brief, GFP positive DP cells from OP9-DL1 co-culture assay were isolated by FACS-sorting (>94% pure). Synthetic miR-223 was spiked into sorted cells at the ratio of 100 μmol of miR-223 per 100,000 cells before RNA purification. Total RNA was isolated using Trizol reagent (Invitrogen, Carlsbad, Calif.). We assumed that the ratio of spiked miR-223 to a miRNA of interest would not change during RNA purification. cDNA was then synthesized using miRNA-specific looped primers (Applied Biosystems, Foster city, Calif.) and amplified with miRNA specific forward primers, TaqMan probe, and reverse primers (Applied Biosystems). PCR amplification was performed in triplicate in an ABI-7000 sequence detection system (Applied Biosystems) at 95° C. for 10 min followed by 40 cycles at 95° C. for 15 sec and 60° C. for 1 min. To determine exact copy number of a miRNA in sorted DP cells, we carried out absolute miRNA quantification with miRNA qPCR assay. Exact copies of test and spiked miRNAs in defined amount of total RNA input were determined by using standard curves for mature miR-181a, miR-181c, and spiked miR-223. miR-181a or miR-181c expression was normalized using miR-15b as internal loading control. Representative results of three miRNA qPCR analyses of independently sorted virally infected DP cells were shown. All reactions were carried out according to the manufacturer's instructions.

Example 6

Synergistic signaling between Notch and pre-TCR pathways is required for thymocyte development and may contribute the pathogenesis of Notch-induced T cell acute lymphoblastic leukemia (T-ALL). However, molecule pathways that mediate the synergy between these two independent signal pathways remain elusive. Here we show that miR-181a, which is highly expressed in both thymic progenitors and T-ALL patients, functions to control early T cell development by dampening of multiple negative regulators involved in both Notch and pre-TCR signaling pathways, including Nrarp (Notch-regulated ankyrin repeat protein) and various phosphatase genes (SHP2, DUSP5, DUSP6, PTPN22). Increase miR-181a expression potentiates the development of CD4 and CD8 double-positive (DP) T cells, whereas genetic and pharmacological ablation of miR-181a inhibits DP cell development.

Moreover, targeted deletion of miR-181a before and after T-ALL onset in a Notch-induced T-ALL mouse model can affect leukemia development and significantly increases overall mice survival. Collectively, these results demonstrate that miR-181a plays a critical role in early T cell development and the pathogenesis of T-ALL by ensuring the synergy between Notch and pre-TCR signaling pathways, and indicate that miR-181a may be an effective therapeutic target for Notch-induced T-ALL.

Figure 21:
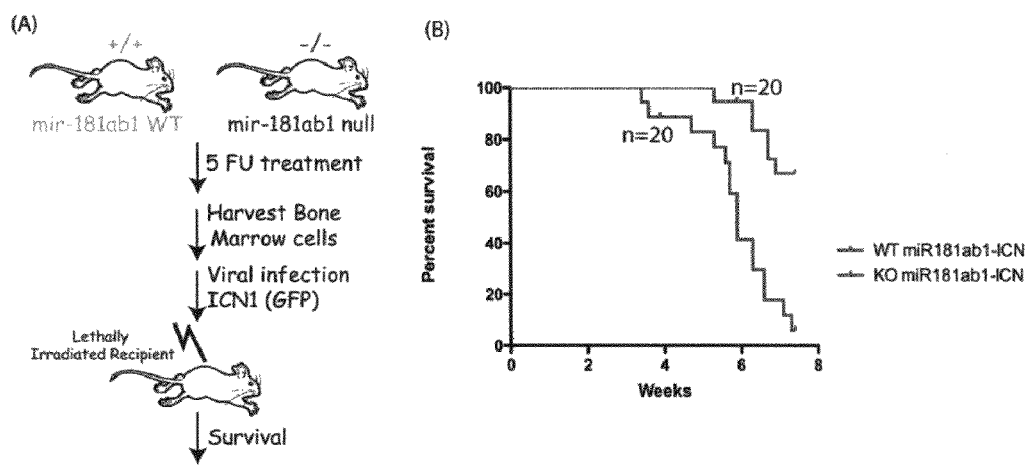
FIG. 21 Mir-181a1b1 contributes to the development of Notch-induced T-ALL in a mouse model.

As shown in FIG. 21, Mir-181a1b1 contributes to the development of Notch-induced T-ALL in a mouse model. (A) Bone marrow cells from wild-type or mir-181a-1/b-1 knockout (KO) mice were infected with retrovirus expressing the Intracellular Notch domain (ICN) and transplanted into lethally irradiated recipients. (B) The survival of recipient mice transplanted with wild-type and mir-181a-1/b-1 KO cells was plotted and Kaplan-Meier method was used to estimate the effects of loss of mir-181a-1/b-1 on the survival of T-ALL mice.

Mir-181a1b1 contributes to maintenance of Notch-induced T-ALL in a mouse model (FIG. 22). (A) Bone marrow cells from wild-type or mir-181a-1/b-1 f/f: CreER mice were infected with retrovirus expressing the Intracellular Notch domain (ICN) and transplanted into lethally irradiated recipients. At 4 weeks post-transplantation, tamoxifen was injected to induced the expression of Cre transgene and the deletion of floxed mir-181a-1/b-1 alleles. (B) The survival of recipient mice transplanted with wild-type and mir-181a-1/b-1 f/f cells was plotted and Kaplan-Meier method was used to estimate the effects of loss of mir-181a-1/b-1 on the survival of T-ALL mice at the onset of T-ALL.

Example 7

Figure 23:
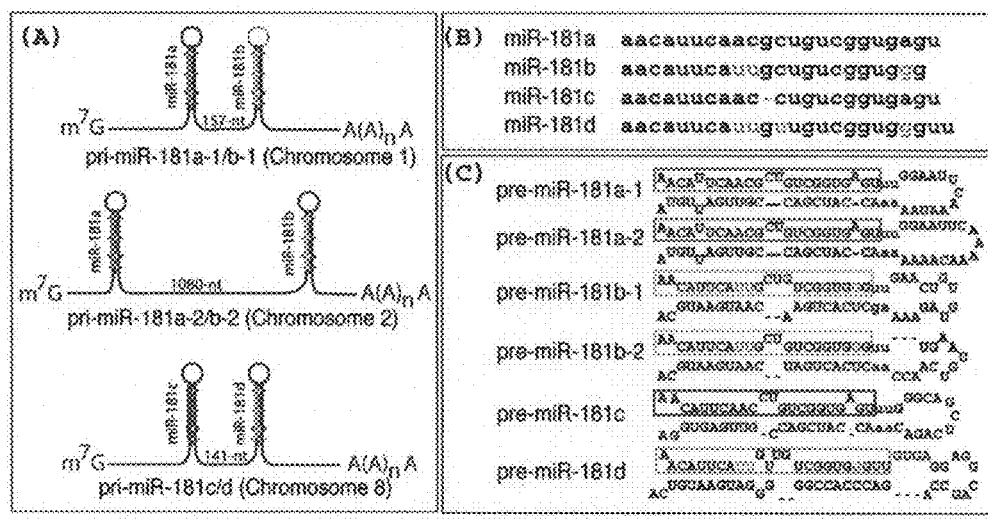
FIG. 23 MiR-181 family miRNAs and their coding genes. (A) Schematics of putative primary miR-181 transcripts. (B) Alignment of mouse mature miR-181 family of miRNAs (SEQ ID NO:1, SEQ ID NO:37, SEQ ID NO:20, SEQ ID NO:38). (C) Predicted stem-loop structures of mature miR-181 family miRNAs (SEQ ID NO:39-44). Mature miRNA sequences are indicated in the box.

We have noted that many miRNA genes are classified into large families consisting of members with highly homologous ~21-nt mature miRNAs. For example, the members of the miR-181 family of genes produce four distinct mature miRNAs (miR-181a, miR-181b, miR-181c, and miR-181d) from three polycistronic miRNA genes: mir-181a-1/b-1, mir-181a-2/b-2, and mir-181c/d, respectively (FIG. 23A-C). The mature miRNAs of the miR-181 family, all with identical 5' seed nucleotides, differ from one another by no more than 3-nt in either the center or 3' end of the mature miRNAs. Particularly, mature miR-181a differs from miR-181c by only one nucleotide in the center of the mature miRNAs (FIG. 23B). According to computational and biochemical analyses, mir-181a-1 and mir-181c, which encode nearly identical mature miRNAs and have identical seed nucleotides (nucleotides 2 through 7 of the mature miRNAs), should be functionally interchangeable. Surprisingly, we found that mir-181a-1, but not mir-181c, can promote early T cell development when ectopically expressed in thymic progenitor cells.

The compositions and procedures provided in the description can be effectively modified by those skilled in the art without departing from the spirit of the invention embodied in the claims that follow.

What is claimed is:

1. A method of inhibiting growth of a T-ALL leukemia, the method comprising:
    contacting said T cell leukemia with an antisense oligonucleotide complementary to miR-181a, wherein the oligonucleotide is at least 12 but not more than 25 nucleotides in length and has no more than 2 mismatches over its length compared to an equal length portion of miR-181a that inhibits the activity of a miR-181a microRNA expressed in said cell wherein the microRNA is a primary or precursor transcript of miR-181a1/b1.

2. The method according to claim 1, wherein the microRNA is a primary or precursor transcript of miR-181a2/b2.

3. The method of claim 1, wherein the microRNA is other than a primary or precursor transcript of miR181c/d.

4. A method of inhibiting growth of a T cell leukemia, the method comprising:
    contacting said T cell leukemia with an antisense oligonucleotide complementary to miR-181a, wherein the oligonucleotide is at least 12 but not more than 25 nucleotides in length and has no more than 2 mismatches over its length compared to an equal length portion of miR-181a that inhibits the activity of a miR-181a microRNA expressed in said cell, wherein said T cell leukemia is T-ALL.

5. A method of inhibiting growth of a T cell leukemia, the method comprising:
    contacting said T cell leukemia with an antisense oligonucleotide complementary to miR-181a, wherein the oligonucleotide is at least 12 but not more than 25 nucleotides in length and has no more than 2 mismatches over its length compared to an equal length portion of miR-181a that inhibits the activity of a miR-181a microRNA expressed in said cell, wherein said T cell leukemia is T-ALL, and wherein said anti-sense oligonucleotide targets nucleotides sequences specific to miR-181a1/b1 that have no overlap with miR181c/d.

6. The method according to claim 4, wherein said inhibiting step is performed in vitro.

7. The method according to claim 4, wherein said inhibiting step is performed in vivo.

* * * * *